(12) United States Patent
de la Torre et al.

(10) Patent No.: US 7,753,928 B2
(45) Date of Patent: Jul. 13, 2010

(54) METHOD AND DEVICE FOR USE IN MINIMALLY INVASIVE PLACEMENT OF INTRAGASTRIC DEVICES

(75) Inventors: Roger de la Torre, Wentzville, MO (US); J. Stephen Scott, St. Charles, MO (US); Thomas A. Howell, Palo Alto, CA (US); George D. Hermann, Portola Valley, CA (US); David Shields, Woodside, CA (US); Robert T. Chang, Belmont, CA (US); Neil Holmgren, Alameda, CA (US); David Willis, Palo Alto, CA (US)

(73) Assignee: Satiety, Inc., Palo Alto, CA (US)

( * ) Notice: Subject to any disclaimer, the term of this patent is extended or adjusted under 35 U.S.C. 154(b) by 1442 days.

(21) Appl. No.: 11/105,835

(22) Filed: Apr. 14, 2005

(65) Prior Publication Data

US 2005/0192615 A1    Sep. 1, 2005

(51) Int. Cl.
*A61M 29/00* (2006.01)
(52) U.S. Cl. .................................. 606/191; 623/23.65
(58) Field of Classification Search ................. 600/101, 600/104; 604/516, 909, 96.01, 192; 606/191, 606/192, 195, 196, 198, 205; 623/23.65, 623/23.64, 23.67, 23.68; 128/898, 899
See application file for complete search history.

(56) References Cited

U.S. PATENT DOCUMENTS

| | | | |
|---|---|---|---|
| 2,108,206 A | 2/1938 | Meeker | |
| 2,508,690 A | 5/1950 | Schmerl | |
| 3,372,443 A | 3/1968 | Daddona, Jr. | |
| 3,395,710 A | 8/1968 | Stratton et al. | |
| 3,884,235 A | * | 5/1975 | Sami ........................ 604/328 |
| 3,986,493 A | 10/1976 | Hendren, III | |
| 4,057,065 A | 11/1977 | Thow | |
| 4,063,561 A | 12/1977 | McKenna | |
| 4,133,315 A | 1/1979 | Berman et al. | |
| 4,134,405 A | 1/1979 | Smit | |
| 4,198,982 A | 4/1980 | Fortner et al. | |
| 4,246,893 A | 1/1981 | Berson | |

(Continued)

FOREIGN PATENT DOCUMENTS

EP    0 137 878 A1    4/1985

(Continued)

OTHER PUBLICATIONS

Büchler, M.W., M.D. et al., A Technique for Gastroplasty As a Substitute for the Esophagus: Fundus Rotation Gastroplasty, *Journal of the American College of Surgeons*, vol. 182, pp. 241-245, Mar. 1996.

(Continued)

*Primary Examiner*—Todd E Manahan
*Assistant Examiner*—David Eastwood
(74) *Attorney, Agent, or Firm*—Fulwider Patton LLP

(57) ABSTRACT

A space occupying device for deployment within a patient's stomach and methods of deploying and removing the device. The device includes an expandable member and fasteners, such as sutures, that extend to least partially through the patient's stomach wall, and that anchor the device with the patient's stomach. The device can be deployed and/or removed through transesophageal approaches and/or through a combination of transesophageal and transabdominal approaches.

8 Claims, 31 Drawing Sheets

U.S. PATENT DOCUMENTS

| | | | |
|---|---|---|---|
| 4,258,705 A | 3/1981 | Sorensen et al. | |
| 4,311,146 A | 1/1982 | Wonder | |
| 4,315,509 A | 2/1982 | Smit | |
| 4,343,066 A | 8/1982 | Lance | |
| 4,402,445 A | 9/1983 | Green | |
| 4,416,267 A | 11/1983 | Garren et al. | |
| 4,458,681 A | 7/1984 | Hopkins | |
| 4,485,805 A * | 12/1984 | Foster, Jr. | 128/898 |
| 4,501,264 A | 2/1985 | Rockey | |
| 4,547,192 A | 10/1985 | Brodsky et al. | |
| 4,558,699 A | 12/1985 | Bashour | |
| 4,592,339 A | 6/1986 | Kuzmak et al. | |
| 4,592,354 A | 6/1986 | Rothfuss | |
| 4,598,699 A | 7/1986 | Garren et al. | |
| 4,607,618 A | 8/1986 | Angelchik | |
| 4,610,383 A | 9/1986 | Rothfuss et al. | |
| 4,636,205 A | 1/1987 | Steer | |
| 4,641,653 A | 2/1987 | Rockey | |
| 4,643,169 A | 2/1987 | Koss et al. | |
| 4,646,722 A | 3/1987 | Silverstein et al. | |
| 4,648,383 A | 3/1987 | Angelchik | |
| 4,671,287 A | 6/1987 | Fiddian-Green | |
| 4,694,827 A * | 9/1987 | Weiner et al. | 606/192 |
| 4,716,900 A | 1/1988 | Ravo et al. | |
| 4,723,547 A | 2/1988 | Kullas et al. | |
| 4,739,758 A | 4/1988 | Lai et al. | |
| 4,744,363 A | 5/1988 | Hasson | |
| 4,773,393 A | 9/1988 | Haber et al. | |
| 4,790,294 A | 12/1988 | Allred, III et al. | |
| 4,795,430 A | 1/1989 | Quinn et al. | |
| 4,803,985 A | 2/1989 | Hill | |
| 4,826,481 A * | 5/1989 | Sacks et al. | 604/516 |
| 4,841,888 A | 6/1989 | Mills et al. | |
| 4,899,747 A | 2/1990 | Garren et al. | |
| 4,905,693 A | 3/1990 | Ravo | |
| 4,925,446 A | 5/1990 | Garay et al. | |
| 4,927,428 A | 5/1990 | Richards | |
| 4,969,474 A | 11/1990 | Schwarz | |
| 5,037,021 A | 8/1991 | Mills et al. | |
| 5,059,193 A | 10/1991 | Kuslich | |
| 5,080,663 A | 1/1992 | Mills et al. | |
| 5,084,061 A | 1/1992 | Gau et al. | |
| 5,112,310 A * | 5/1992 | Grobe | 604/175 |
| 5,129,915 A | 7/1992 | Cantenys | |
| 5,156,609 A | 10/1992 | Nakao et al. | |
| 5,167,627 A * | 12/1992 | Clegg et al. | 604/103.03 |
| 5,171,233 A | 12/1992 | Amplatz et al. | |
| 5,197,649 A | 3/1993 | Bessler et al. | |
| 5,220,928 A | 6/1993 | Oddsen et al. | |
| 5,222,961 A | 6/1993 | Nakao et al. | |
| 5,226,429 A | 7/1993 | Kuzmak | |
| 5,234,454 A * | 8/1993 | Bangs | 606/191 |
| 5,246,456 A | 9/1993 | Wilkinson | |
| 5,248,302 A | 9/1993 | Patrick et al. | |
| 5,250,058 A | 10/1993 | Miller et al. | |
| 5,254,126 A | 10/1993 | Filipi et al. | |
| 5,259,366 A | 11/1993 | Reydel et al. | |
| 5,259,399 A * | 11/1993 | Brown | 128/897 |
| 5,261,920 A | 11/1993 | Main et al. | |
| 5,263,629 A | 11/1993 | Trumbull et al. | |
| 5,297,536 A | 3/1994 | Wilk | |
| 5,301,658 A | 4/1994 | Zhu et al. | |
| 5,306,300 A | 4/1994 | Berry | |
| 5,309,896 A | 5/1994 | Moll et al. | |
| 5,309,927 A | 5/1994 | Welch | |
| 5,327,914 A | 7/1994 | Shlain | |
| 5,330,486 A | 7/1994 | Wilk | |
| 5,330,503 A | 7/1994 | Yoon | |
| 5,331,975 A | 7/1994 | Bonutti | |
| 5,334,209 A | 8/1994 | Yoon | |
| 5,334,210 A | 8/1994 | Gianturco | |
| 5,345,949 A | 9/1994 | Shlain | |
| 5,346,501 A | 9/1994 | Regula et al. | |
| 5,355,897 A | 10/1994 | Pietrafitta et al. | |
| 5,376,095 A | 12/1994 | Ortiz | |
| 5,382,231 A | 1/1995 | Shlain | |
| 5,403,312 A | 4/1995 | Yates et al. | |
| 5,403,326 A | 4/1995 | Harrison et al. | |
| 5,411,508 A | 5/1995 | Bessler et al. | |
| 5,433,721 A | 7/1995 | Hooven et al. | |
| 5,437,291 A | 8/1995 | Pasricha et al. | |
| 5,449,368 A | 9/1995 | Kuzmak | |
| 5,452,837 A | 9/1995 | Williamson, IV et al. | |
| 5,458,131 A | 10/1995 | Wilk | |
| 5,465,894 A | 11/1995 | Clark et al. | |
| 5,467,911 A | 11/1995 | Tsuruta et al. | |
| 5,486,183 A | 1/1996 | Middleman et al. | |
| 5,489,058 A | 2/1996 | Plyley et al. | |
| 5,503,635 A | 4/1996 | Sauer et al. | |
| 5,527,319 A | 6/1996 | Green et al. | |
| 5,535,935 A | 7/1996 | Vidal et al. | |
| 5,542,949 A | 8/1996 | Yoon | |
| 5,549,621 A | 8/1996 | Bessler et al. | |
| 5,551,622 A | 9/1996 | Yoon | |
| 5,555,898 A | 9/1996 | Suzuki et al. | |
| 5,558,665 A | 9/1996 | Kieturakis | |
| 5,571,116 A | 11/1996 | Bolanos et al. | |
| 5,577,654 A | 11/1996 | Bishop | |
| 5,578,044 A | 11/1996 | Gordon et al. | |
| 5,582,616 A | 12/1996 | Bolduc et al. | |
| 5,584,861 A | 12/1996 | Swain et al. | |
| 5,588,579 A | 12/1996 | Schnut et al. | |
| 5,601,604 A | 2/1997 | Vincent | |
| 5,603,443 A | 2/1997 | Clark et al. | |
| 5,607,094 A | 3/1997 | Clark et al. | |
| 5,624,381 A | 4/1997 | Kieturakis | |
| 5,626,588 A | 5/1997 | Sauer et al. | |
| 5,639,008 A | 6/1997 | Gallagher et al. | |
| 5,649,937 A | 7/1997 | Bito et al. | |
| 5,651,769 A | 7/1997 | Waxman et al. | |
| 5,655,698 A | 8/1997 | Yoon | |
| 5,662,664 A | 9/1997 | Gordon et al. | |
| 5,662,667 A | 9/1997 | Knodel | |
| 5,667,520 A | 9/1997 | Bonutti | |
| 5,676,659 A | 10/1997 | McGurk | |
| 5,676,674 A | 10/1997 | Bolanos et al. | |
| 5,685,868 A | 11/1997 | Lundquist | |
| 5,690,656 A | 11/1997 | Cope et al. | |
| 5,697,943 A | 12/1997 | Sauer et al. | |
| 5,707,382 A | 1/1998 | Sierocuk et al. | |
| 5,722,990 A | 3/1998 | Sugarbaker et al. | |
| 5,728,178 A | 3/1998 | Buffington et al. | |
| 5,735,848 A | 4/1998 | Yates et al. | |
| 5,749,893 A | 5/1998 | Vidal et al. | |
| 5,755,730 A | 5/1998 | Swain et al. | |
| 5,766,216 A | 6/1998 | Gangal et al. | |
| 5,776,054 A | 7/1998 | Bobra | |
| 5,782,844 A | 7/1998 | Yoon et al. | |
| 5,788,715 A | 8/1998 | Watson, Jr. et al. | |
| 5,792,153 A | 8/1998 | Swain et al. | |
| 5,797,931 A | 8/1998 | Bito et al. | |
| 5,810,851 A | 9/1998 | Yoon | |
| 5,810,855 A | 9/1998 | Rayburn et al. | |
| 5,810,882 A | 9/1998 | Bolduc et al. | |
| 5,816,471 A | 10/1998 | Plyley et al. | |
| 5,820,584 A | 10/1998 | Crabb | |
| 5,824,008 A | 10/1998 | Bolduc et al. | |
| 5,827,298 A | 10/1998 | Hart et al. | |
| 5,833,690 A | 11/1998 | Yates et al. | |
| 5,836,311 A | 11/1998 | Borst et al. | |
| 5,839,639 A | 11/1998 | Sauer et al. | |
| 5,860,581 A | 1/1999 | Robertson et al. | |
| 5,861,036 A | 1/1999 | Godin | |
| 5,868,141 A | 2/1999 | Ellias | |

| | | | | | | |
|---|---|---|---|---|---|---|
| 5,868,760 | A | 2/1999 | McGuckin, Jr. | 6,506,196 B1 | 1/2003 | Laufer |
| 5,876,448 | A | 3/1999 | Thompson et al. | 6,535,764 B2 | 3/2003 | Imran et al. |
| 5,879,371 | A | 3/1999 | Gardiner et al. | 6,540,789 B2 | 4/2003 | Silverman et al. |
| 5,887,594 | A | 3/1999 | LoCicero, III | 6,551,310 B1 | 4/2003 | Ganz et al. |
| 5,888,196 | A | 3/1999 | Bonutti | 6,554,844 B2 | 4/2003 | Lee et al. |
| 5,897,534 | A | 4/1999 | Heim et al. | 6,558,400 B2 | 5/2003 | Deem et al. |
| 5,897,562 | A | 4/1999 | Bolanos et al. | 6,561,969 B2 | 5/2003 | Frazier et al. |
| 5,904,147 | A | 5/1999 | Conlan et al. | 6,572,629 B2 | 6/2003 | Kalloo et al. |
| 5,906,625 | A | 5/1999 | Bito et al. | 6,592,596 B1 | 7/2003 | Geitz |
| 5,910,105 | A | 6/1999 | Swain et al. | 6,605,037 B1 | 8/2003 | Gresl, Jr. et al. |
| 5,910,149 | A | 6/1999 | Kuzmak | 6,626,899 B2 | 9/2003 | Houser et al. |
| 5,921,993 | A | 7/1999 | Yoon | 6,632,227 B2 | 10/2003 | Adams |
| 5,927,284 | A | 7/1999 | Borst et al. | 6,663,598 B1 | 12/2003 | Carrillo, Jr. et al. |
| 5,928,264 | A | 7/1999 | Sugarbaker et al. | 6,663,639 B1 | 12/2003 | Laufer et al. |
| 5,935,107 | A | 8/1999 | Taylor et al. | 6,663,640 B2 | 12/2003 | Kortenbach |
| 5,938,669 | A | 8/1999 | Klaiber et al. | 6,675,809 B2 | 1/2004 | Stack et al. |
| 5,947,983 | A | 9/1999 | Solar et al. | 6,682,520 B2 | 1/2004 | Ingenito |
| 5,964,772 | A | 10/1999 | Bolduc et al. | 6,689,062 B1 | 2/2004 | Mesallum |
| 5,964,782 | A | 10/1999 | Lafontaine et al. | 6,692,485 B1 | 2/2004 | Brock et al. |
| 5,972,001 | A | 10/1999 | Yoon | 6,716,222 B2 | 4/2004 | McAlister et al. |
| 5,972,002 | A | 10/1999 | Bark et al. | 6,733,512 B2 | 5/2004 | McGhan |
| 5,976,161 | A | 11/1999 | Kirsch et al. | 6,736,822 B2 | 5/2004 | McClellan et al. |
| 5,980,537 | A | 11/1999 | Ouchi | 6,740,098 B2 | 5/2004 | Abrams et al. |
| 5,993,464 | A | 11/1999 | Knodel | 6,740,121 B2 | 5/2004 | Geitz |
| 5,993,473 | A * | 11/1999 | Chan et al. .................. 606/192 | 6,746,489 B2 | 6/2004 | Dua et al. |
| 6,015,378 | A | 1/2000 | Borst et al. | 6,754,536 B2 | 6/2004 | Swoyer et al. |
| 6,030,364 | A | 2/2000 | Durgin et al. | 6,755,849 B1 | 6/2004 | Gowda et al. |
| 6,030,392 | A | 2/2000 | Dakov | 6,755,869 B2 | 6/2004 | Geitz |
| 6,042,538 | A | 3/2000 | Puskas | 6,756,364 B2 | 6/2004 | Barbier et al. |
| 6,044,847 | A | 4/2000 | Carter et al. | 6,764,518 B2 | 7/2004 | Godin |
| 6,067,991 | A | 5/2000 | Forsell | 6,773,440 B2 | 8/2004 | Gannoe et al. |
| 6,074,343 | A | 6/2000 | Nathanson et al. | 6,773,441 B1 | 8/2004 | Laufer et al. |
| 6,083,241 | A | 7/2000 | Longo et al. | 6,786,898 B2 | 9/2004 | Guenst |
| 6,086,600 | A | 7/2000 | Kortenbach | 6,790,214 B2 | 9/2004 | Kraemer et al. |
| 6,113,609 | A | 9/2000 | Adams | 6,802,868 B2 | 10/2004 | Silverman et al. |
| 6,119,913 | A | 9/2000 | Adams et al. | 6,821,285 B2 | 11/2004 | Laufer et al. |
| 6,120,513 | A | 9/2000 | Bailey et al. | 6,835,199 B2 | 12/2004 | McGuckin, Jr. et al. |
| 6,136,006 | A | 10/2000 | Johnson et al. | 6,835,200 B2 | 12/2004 | Laufer et al. |
| 6,159,146 | A | 12/2000 | El Gazayerli | 6,837,848 B2 | 1/2005 | Bonner et al. |
| 6,159,195 | A | 12/2000 | Ha et al. | 6,840,423 B2 | 1/2005 | Adams et al. |
| 6,165,183 | A | 12/2000 | Kuehn et al. | 6,845,776 B2 | 1/2005 | Stack et al. |
| 6,179,195 | B1 | 1/2001 | Adams et al. | 6,896,682 B1 | 5/2005 | McClellan et al. |
| 6,186,942 | B1 | 2/2001 | Sullivan et al. | 6,926,722 B2 | 8/2005 | Geitz |
| 6,186,985 | B1 | 2/2001 | Snow | 6,966,919 B2 | 11/2005 | Sixto, Jr. et al. |
| 6,197,022 | B1 | 3/2001 | Baker | 6,981,978 B2 | 1/2006 | Gannoe |
| 6,200,318 | B1 | 3/2001 | Har-Shai et al. | 6,991,643 B2 | 1/2006 | Saadat |
| 6,206,822 | B1 | 3/2001 | Foley et al. | 7,020,531 B1 | 3/2006 | Colliou et al. |
| 6,206,893 | B1 | 3/2001 | Klein et al. | 7,025,791 B2 | 4/2006 | Levine et al. |
| 6,224,614 | B1 | 5/2001 | Yoon | 7,033,378 B2 | 4/2006 | Smith et al. |
| 6,231,561 | B1 | 5/2001 | Frazier et al. | 7,037,343 B2 | 5/2006 | Imran |
| 6,248,058 | B1 | 6/2001 | Silverman et al. | 7,037,344 B2 | 5/2006 | Kagan et al. |
| 6,254,642 | B1 | 7/2001 | Taylor | 7,063,715 B2 | 6/2006 | Onuki et al. |
| 6,273,897 | B1 | 8/2001 | Dalessandro et al. | 7,083,630 B2 | 8/2006 | DeVries et al. |
| 6,279,809 | B1 | 8/2001 | Nicolo | 7,087,011 B2 | 8/2006 | Cabiri et al. |
| 6,290,674 | B1 | 9/2001 | Roue et al. | 7,097,650 B2 | 8/2006 | Weller et al. |
| 6,293,923 | B1 | 9/2001 | Yachia et al. | 2001/0014800 A1 | 8/2001 | Frazier et al. |
| 6,302,917 | B1 | 10/2001 | Dua et al. | 2001/0020190 A1 | 9/2001 | Taylor |
| 6,312,437 | B1 | 11/2001 | Kortenbach | 2001/0037127 A1 | 11/2001 | De Hoyos Garza |
| 6,328,689 | B1 | 12/2001 | Gonzalez et al. | 2002/0022851 A1 | 2/2002 | Kalloo et al. |
| 6,338,345 | B1 | 1/2002 | Johnson et al. | 2002/0035361 A1 | 3/2002 | Houser et al. |
| 6,352,543 | B1 | 3/2002 | Cole | 2002/0040226 A1 | 4/2002 | Laufer et al. |
| 6,358,197 | B1 | 3/2002 | Silverman et al. | 2002/0047036 A1 | 4/2002 | Sullivan et al. |
| 6,379,366 | B1 | 4/2002 | Fleischman et al. | 2002/0058967 A1 | 5/2002 | Jervis |
| 6,387,104 | B1 | 5/2002 | Pugsley, Jr. et al. | 2002/0072761 A1 | 6/2002 | Abrams et al. |
| 6,398,795 | B1 | 6/2002 | McAlister et al. | 2002/0077661 A1 | 6/2002 | Saadat |
| 6,416,535 | B1 | 7/2002 | Lazarus | 2002/0078967 A1 | 6/2002 | Sixto, Jr. et al. |
| 6,423,087 | B1 | 7/2002 | Sawada | 2002/0082621 A1 | 6/2002 | Schurr et al. |
| 6,432,040 | B1 | 8/2002 | Meah | 2002/0143346 A1 | 10/2002 | McGuckin, Jr. et al. |
| 6,447,533 | B1 | 9/2002 | Adams | 2002/0165589 A1 | 11/2002 | Imran et al. |
| 6,460,543 | B1 | 10/2002 | Forsell | 2002/0183768 A1 | 12/2002 | Deem et al. |
| 6,475,136 | B1 | 11/2002 | Forsell | 2002/0193816 A1 | 12/2002 | Laufer et al. |
| 6,491,707 | B2 | 12/2002 | Makower et al. | 2003/0040804 A1 | 2/2003 | Stack et al. |
| 6,494,888 | B1 | 12/2002 | Laufer et al. | 2003/0040808 A1 | 2/2003 | Stack et al. |

| | | |
|---|---|---|
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0022305 A1 | 2/2004 | Tzannes |
| 2004/0024386 A1 | 2/2004 | Deem et al. |
| 2004/0037865 A1 | 2/2004 | Miller |
| 2004/0039452 A1 | 2/2004 | Bessler |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat et al. |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0225183 A1 | 11/2004 | Michlitsch et al. |
| 2004/0225194 A1 | 11/2004 | Smith et al. |
| 2005/0021681 A1 | 1/2005 | Oommen |
| 2005/0038415 A1 | 2/2005 | Rohr et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0203548 A1 | 9/2005 | Weller et al. |
| 2005/0228415 A1 | 10/2005 | Gertner |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |

FOREIGN PATENT DOCUMENTS

| | | |
|---|---|---|
| EP | 0137878 A1 | 4/1985 |
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |
| WO | 88/00027 A1 | 1/1988 |
| WO | WO 94/18893 A1 | 9/1994 |
| WO | WO 97/23157 | 3/1997 |
| WO | WO 99/17662 A1 | 4/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A2 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |

WO WO 2006/078781 A1 7/2006

OTHER PUBLICATIONS

Chang, Craig G. M.D.[1], et al.. Gastro-Clip® Gastroplasty: A Very Long-Term Complication, *Obesity Surgery*, 14, © FD-Communications Inc.. 2004.

Endo Gia* Universal, Single UseStapler and Endo Gia Roticulator*, Brochure, 8 pages, Undated.

Filipi, Charles J. M.D., et al., Transoral, Flexible Endoscopic Suturing for Treatment of GERD: A Multicenter Trial, *Gastrointestinal Endoscopy*,. vol. 53, No. 4, pp. 416-422, 2001.

Guidant, Internet, Axius™ Vacuum 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print pp. 1-20, Medscape General Medicine 4(1), 2003 © 2002 Medscape, downloaded Oct. 9, 2006.

Hepworth, Clive C. FRCS et al., Mechanical Endoscopic Methods of Haemostasis for Bleeding Peptic Ulcers: A Review, *Bailliere's Clinical Gastroenterology*, vol. 14, No. 3 pp. 467-476, 2000.

Ikeda, Y. et al., New Suturing Device for Transanal Endoscopic Microsurgery, *Blackwell Science Ltd*. p. 1290, 1997.

Johnson & Johnson Gateway[sm] Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor, Appendix F.f, Undated.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing and Stapling Machines, *Endoscopy* pp. 205-210, © Georg Thieme Verlag Stuttgart, New York, 1997.

Swain, C. Paul, M.D. et al., An Endoscopic Stapling Device: The Development of a New Endoscopically Controlled Device for Placing Multiple Transmural Staples in Gastrointestinal Tissue, *Gastrointestinal Endoscopy*, vol. 35, No. 4, pp. 338-339, 1989.

Swain, C. Paul, M.D., Endoscopic Suturing, *Bailliere's Clinical Gastroenterology*, Bailliere's Tindall,, vol. 13 No. 1, pp. 97-108, 1999.

Vandenplas, Y., et al., Intragastric Balloons in Adolescents With Morbid Obesity, *European Journal of Gastroenterology & Hepatology*, vol. 11, No. 3, pp. 243-245, 1999.

T. M. Boyle et al., "Small Intestinal Obstruction Secondary to Obturation by a Garren Gastric Bubble", *The Am. J. of Gastroenterology*, vol. 82, No. 1, 1987, pp. 51-53.

C. Clark, "The Gastric Bubble: Medicine, Magic or Mania?", *SGA J.*, vol. 9, No. 2, 1986, 45-47.

S. L. Edell et al., "Radiographic Evaluation of the Garren Gastric Bubble," *AJR* 145, 1985, pp. 49-50.

D. F. Kirby et al., "Incomplete Small Bowel Obstruction by the Garren-Edwards Gastric Bubble Necessitating Surgical Intervention", *The Am. J. of Gastroenterology*, vol. 82, No. 3, 1987, pp. 251-253.

O. G. Nieben et al., "Intragastric ballon as an artificial bezoar for treatment of obesity", The Lancet, Mar. 27, 1982, pp. 198-199.

T. V. Taylor et al., "Gastric Baloons for Obesity", The Lancet, Mar. 27, 1982, p. 750.

W. L. Percival, MD, "The Balloon Diet": a Noninvasive Treatment for Morbid Obesity. Preliminary Report of 108 Patients, *The Canadian J. of Surgery*, vol. 27, No. 2, 1984, pp. 135-136.

Y. Vandenplas et al., "Intragastric balloons in adolescents with morbid obesity", *European J. of Gastroenterology & Hepatology*, vol. 11, No. 3. pp. 243-245, 1999.

B. De Waele, MD et al., "Inragastric Balloons for Preoperative Weight Reduction", *Obesity Surgery*, 10, pp. 58-60, 2000.

S. B. Benjamin et al., Abstract, "A Double-Blind Cross Over Study of the Garren-Edwards Anti-Obesity Bubble", *Gastrointestinal Endoscopy*, 1987, Abstract No. 105, vol. 33, No. 2, 1987, p. 168.

S. B. Benjamin, Abstract, "Small Bowel Obstruction and the Garren-Edwards Bubble: Lessons to be Learned?", *Gastrointestinal Endoscopy*, Abstract No. 161, vol. 33, No. 2, 1987, p. 183.

O. W. Cass, Abstract, "Long-Term Follow-Up of Patients with Percutaneous Endoscopic Gastrostomy", *Gastrointestinal Endoscopy*, Abstract No. 162, vol. 33, No. 2, 1987, p. 183.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W. Ph.D. D.Sc., *Physiology of the Digestive Tract: An Introductory Text*, 3d Ed., Cover and Table of Contents, 1971.

DeMeester, Tom T., M.D., Evolving Concepts of Reflux: The Ups and Downs of the LES, *Canadian Journal of Gastroenterology*, vol. 16, No. 5, pp. 327-331, 2002.

Gray, Henry, R.R.S., *Anatomy of the Human Body*, The Digestive System, Thirtieth American Edition, pp. 1466-1467 (Undated).

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

U.S. Appl. No. 10/773,883, filed Feb. 5, 2004 unpublished; Inventors: Gerbi et al.

U.S. Appl. No. 10/797,439, filed Mar. 9, 2004 unpublished; Inventors: Weller et al.

* cited by examiner

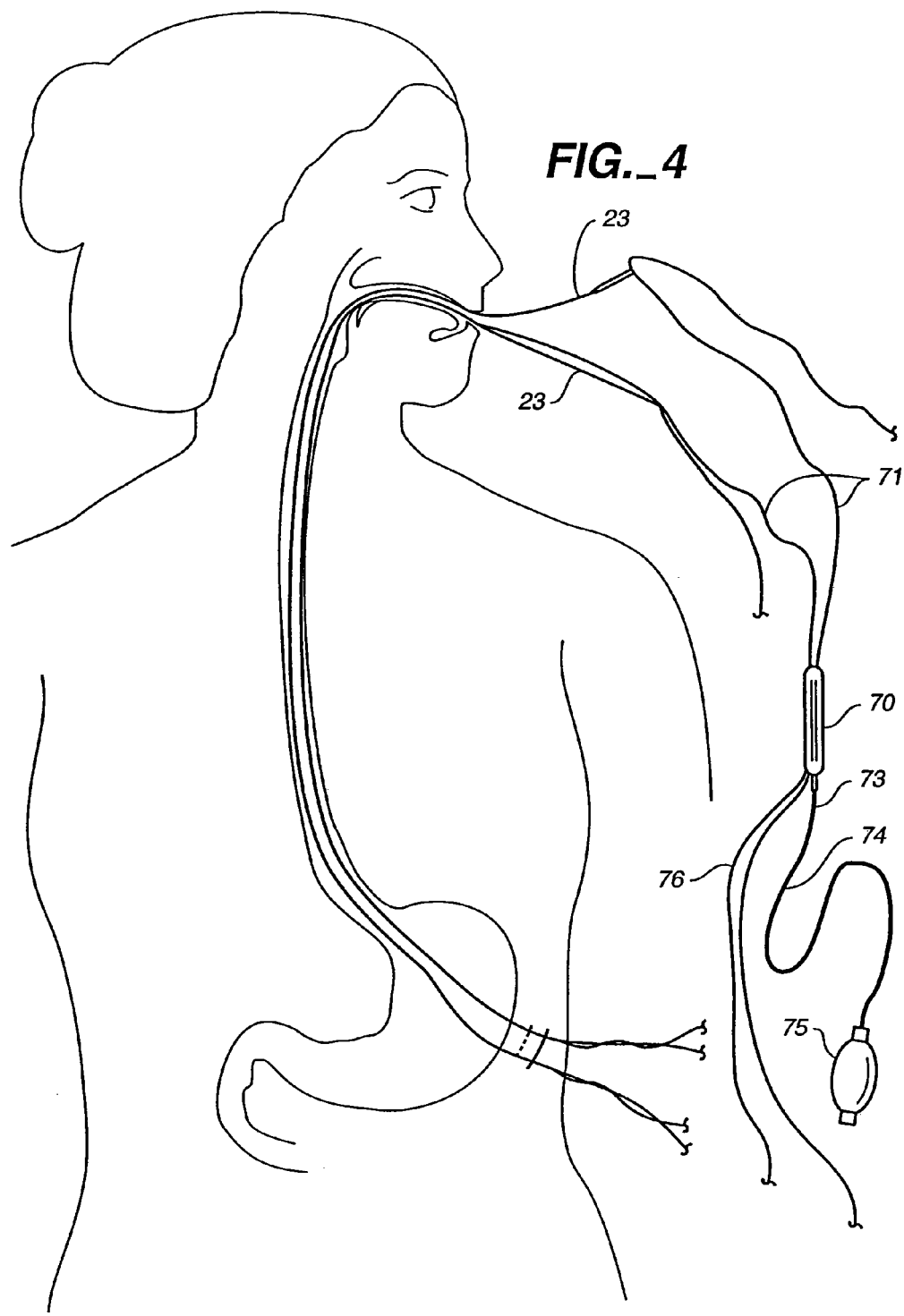

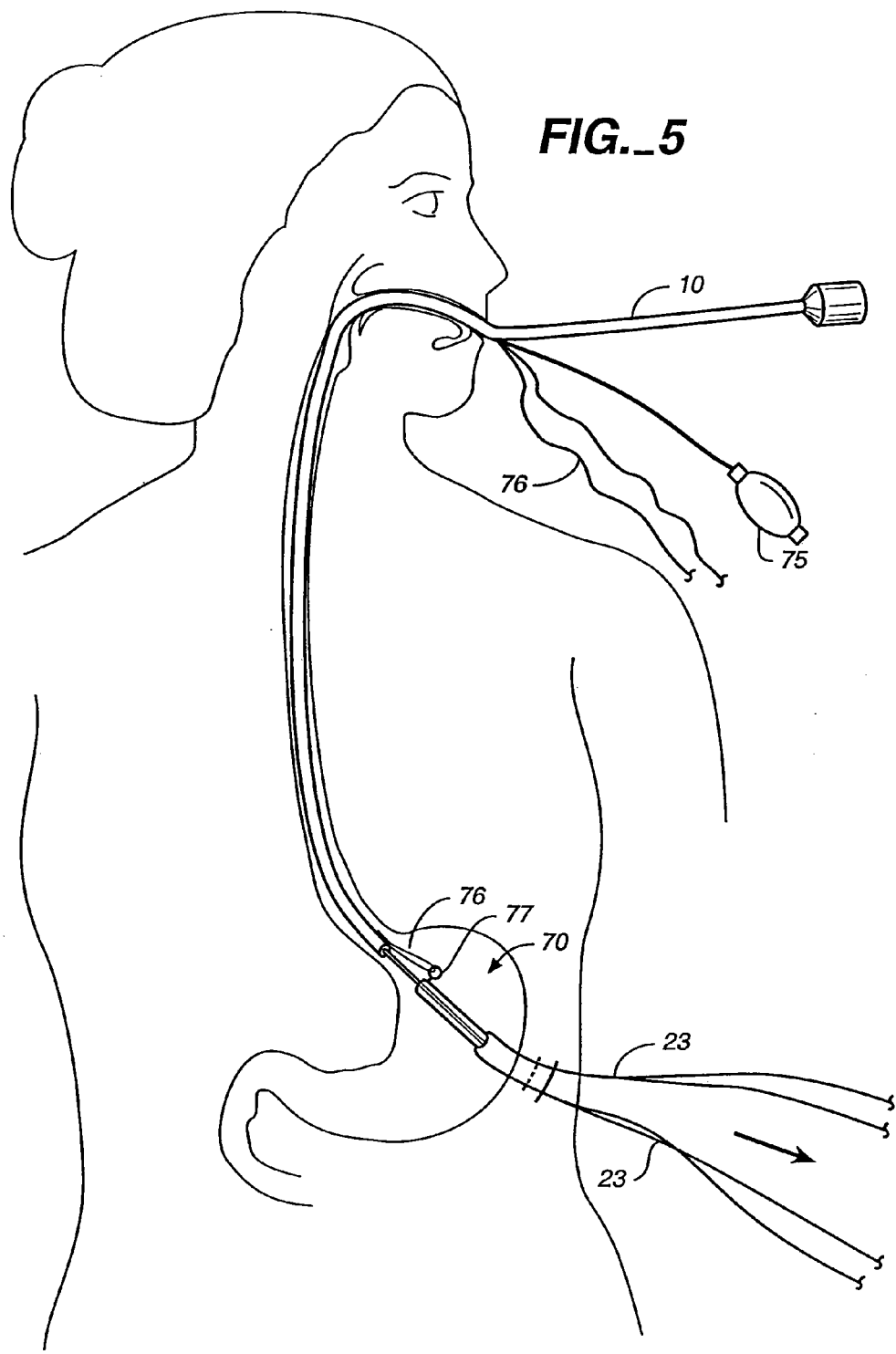
FIG._5

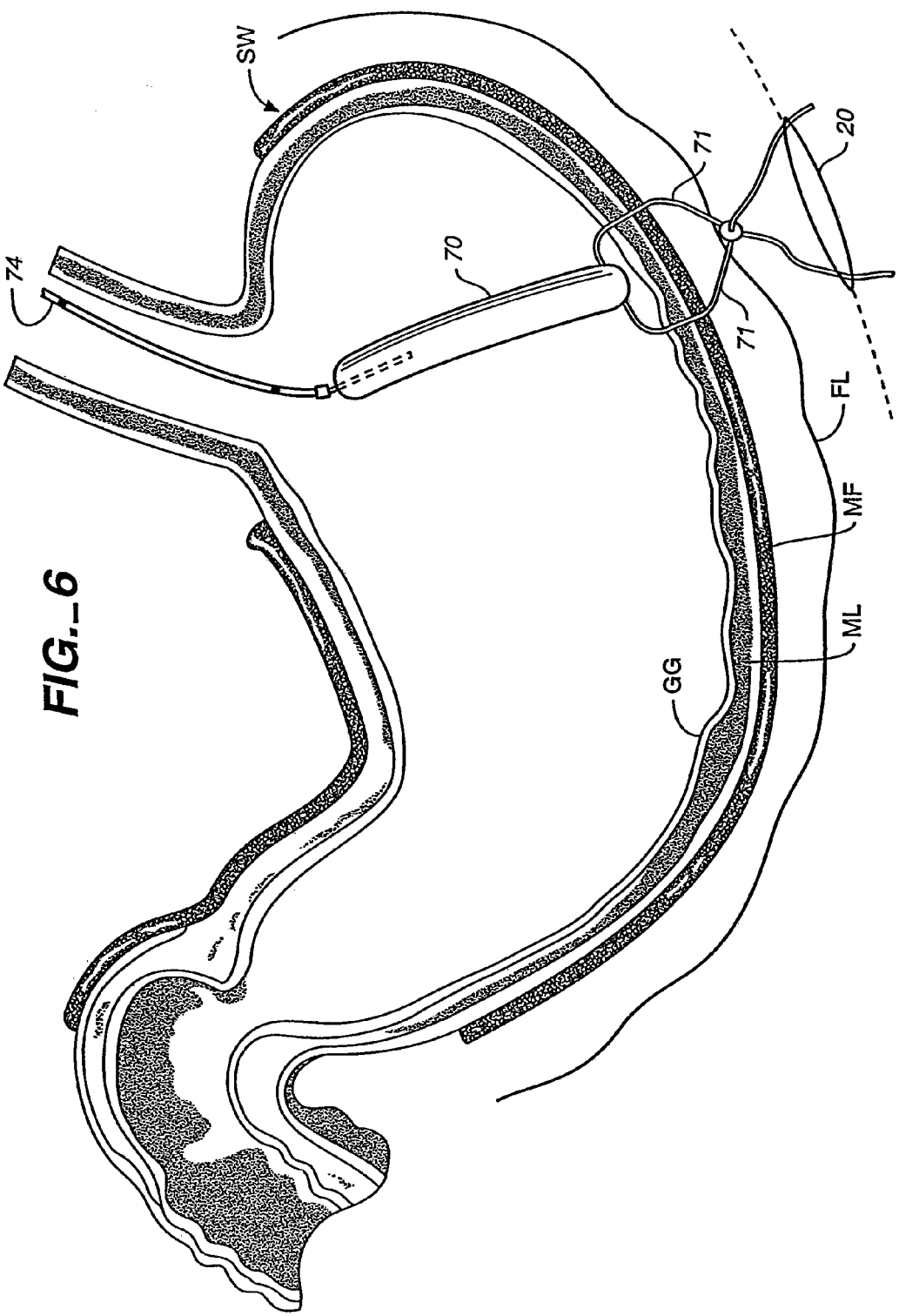
FIG._6

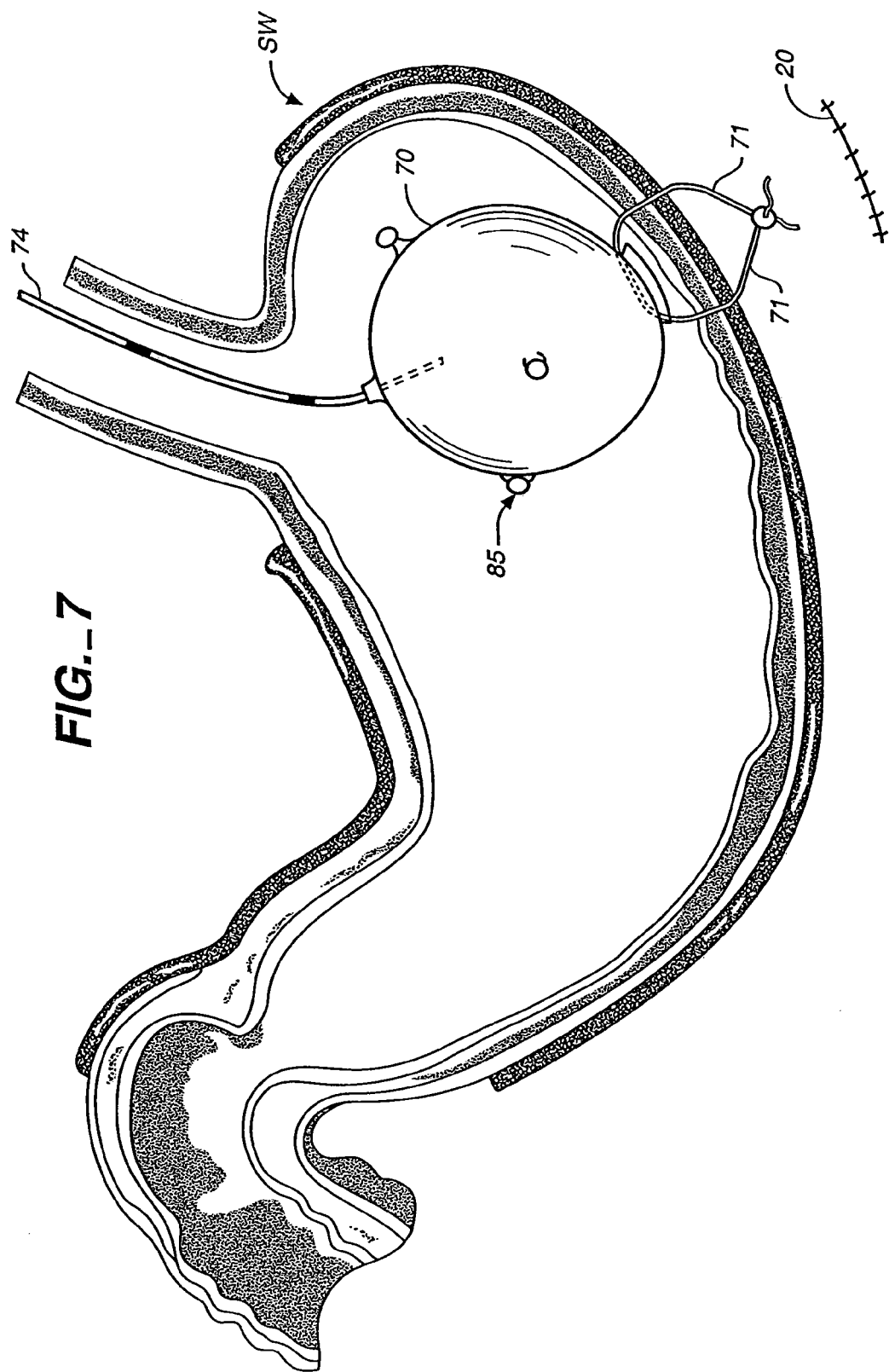
FIG._7

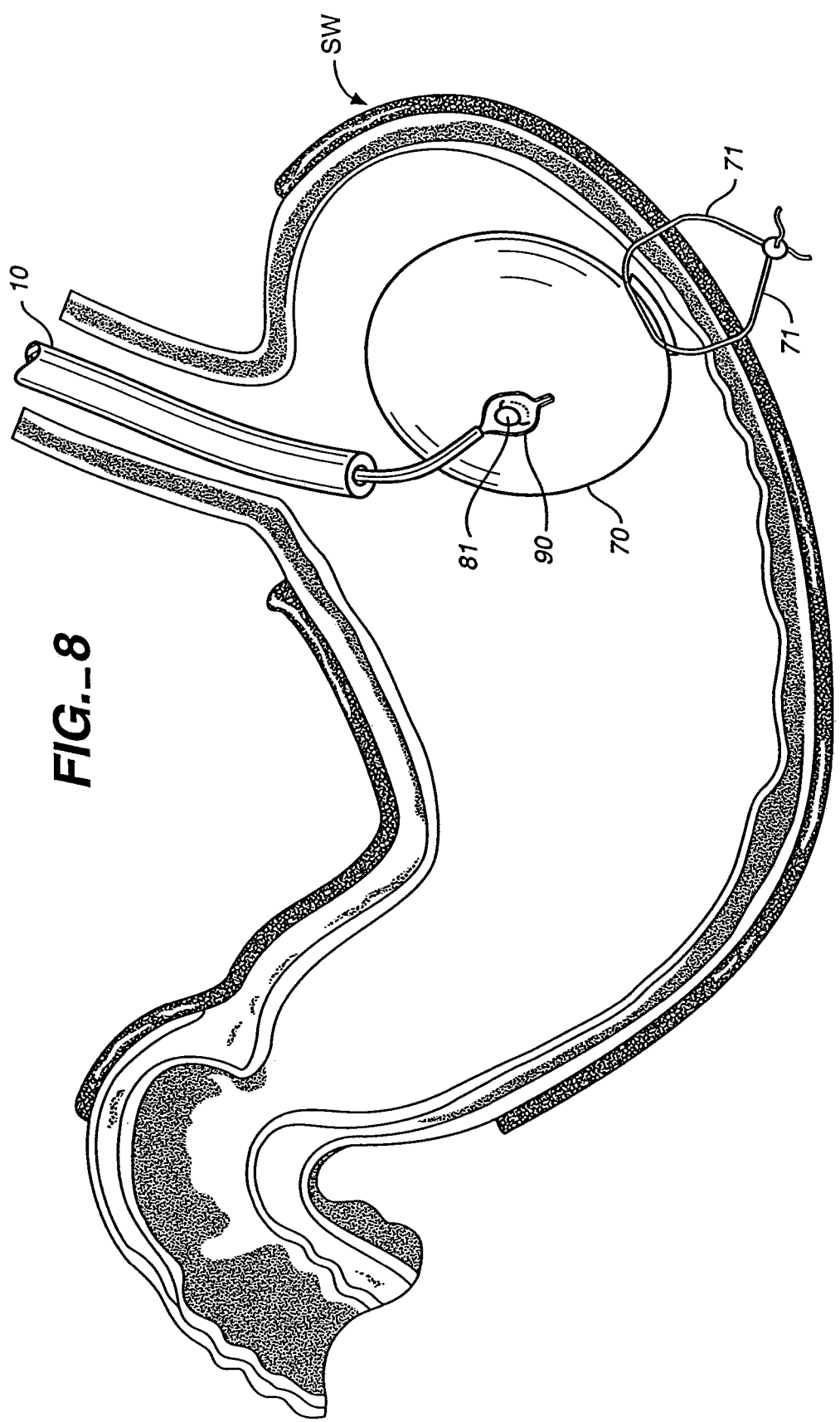

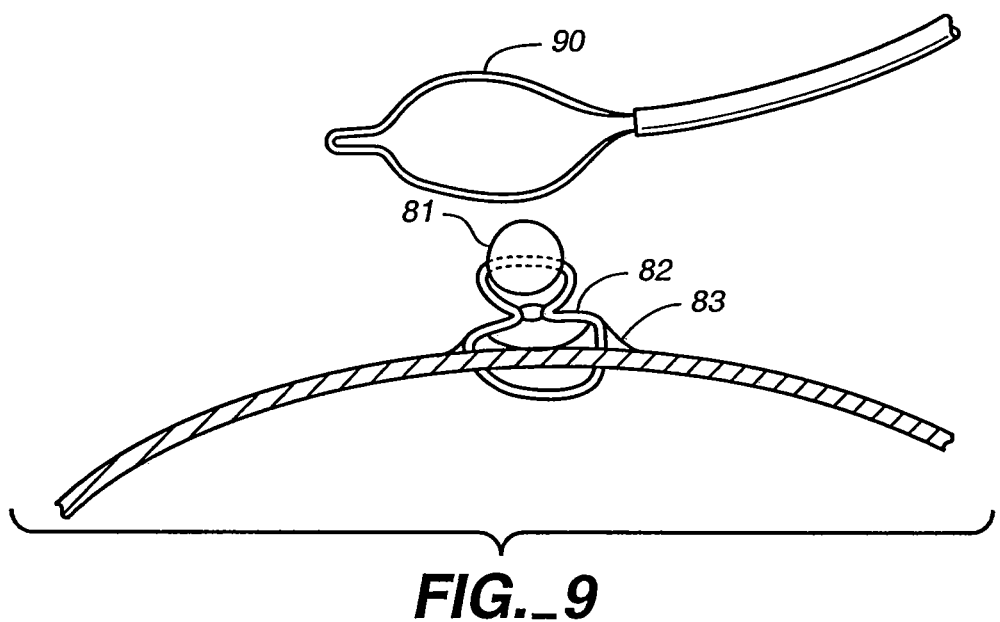
FIG._9
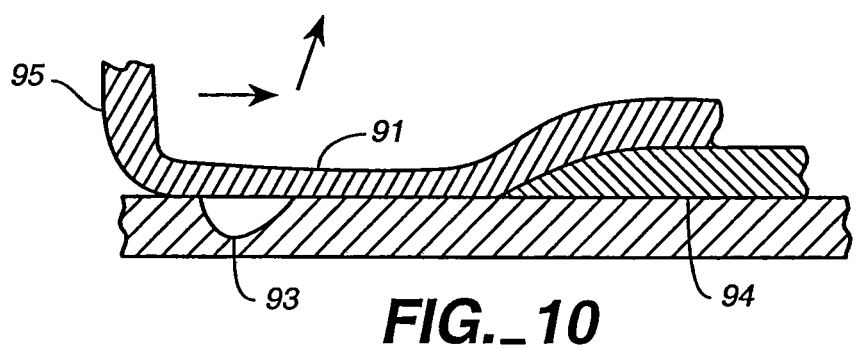
FIG._10

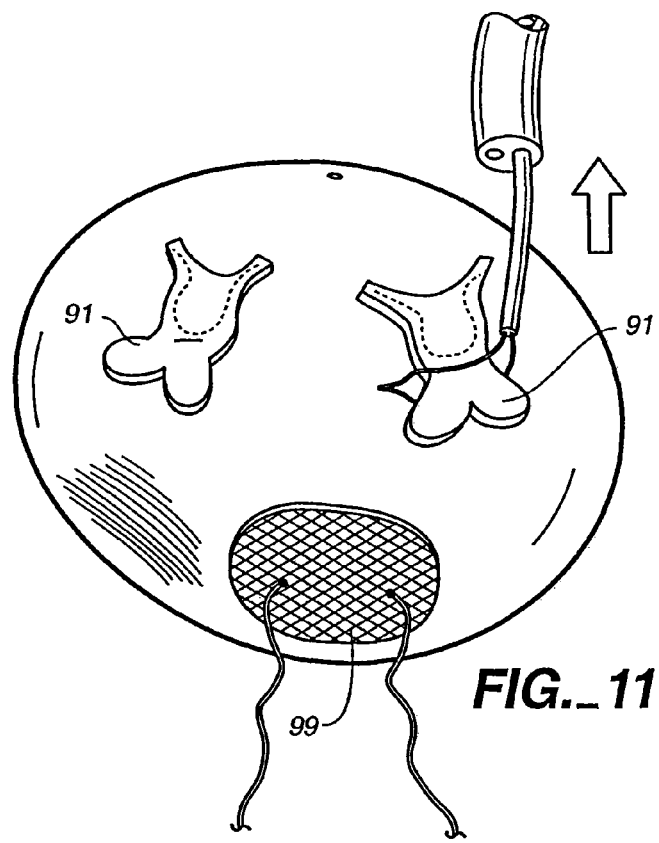
FIG._11
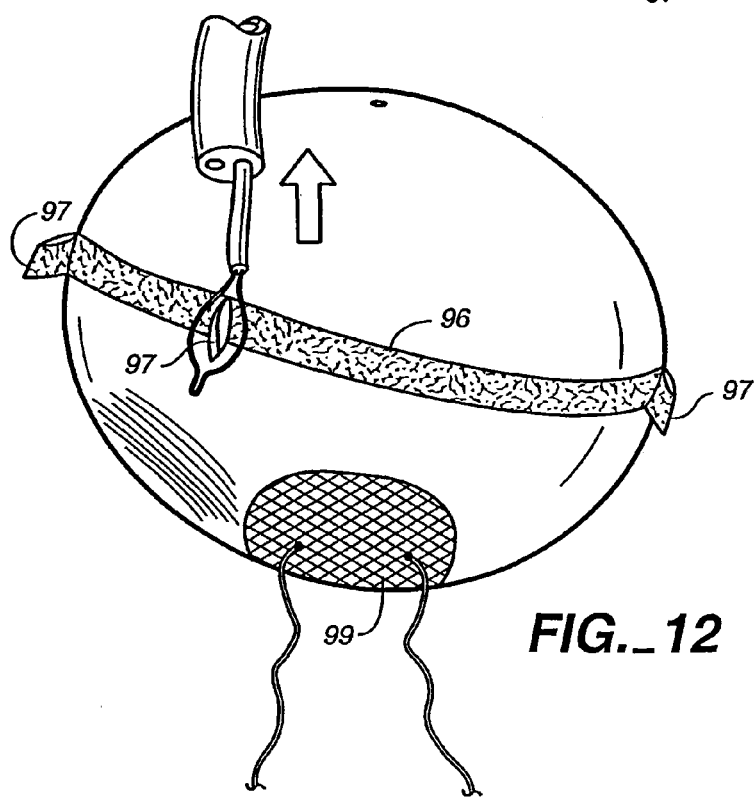
FIG._12

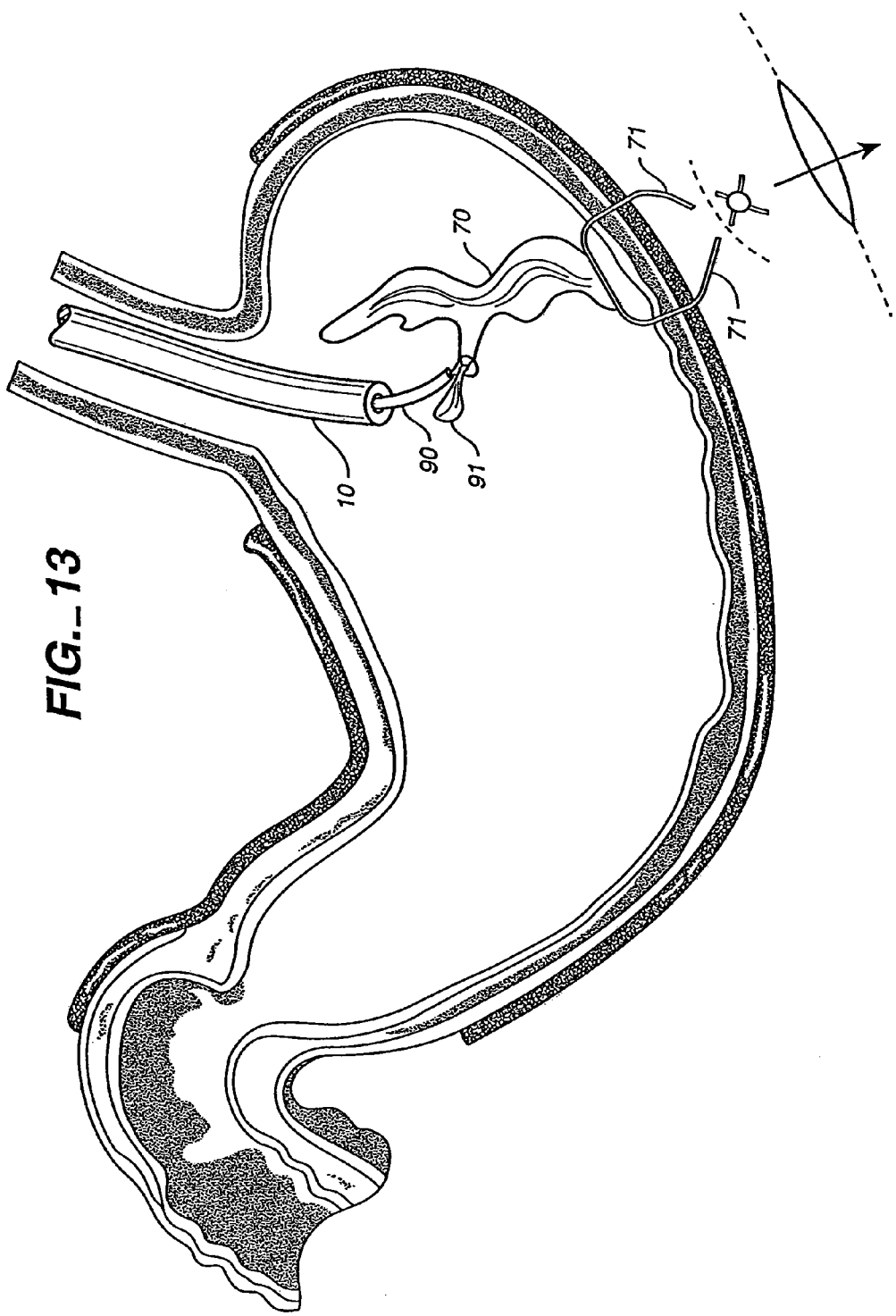
FIG._13

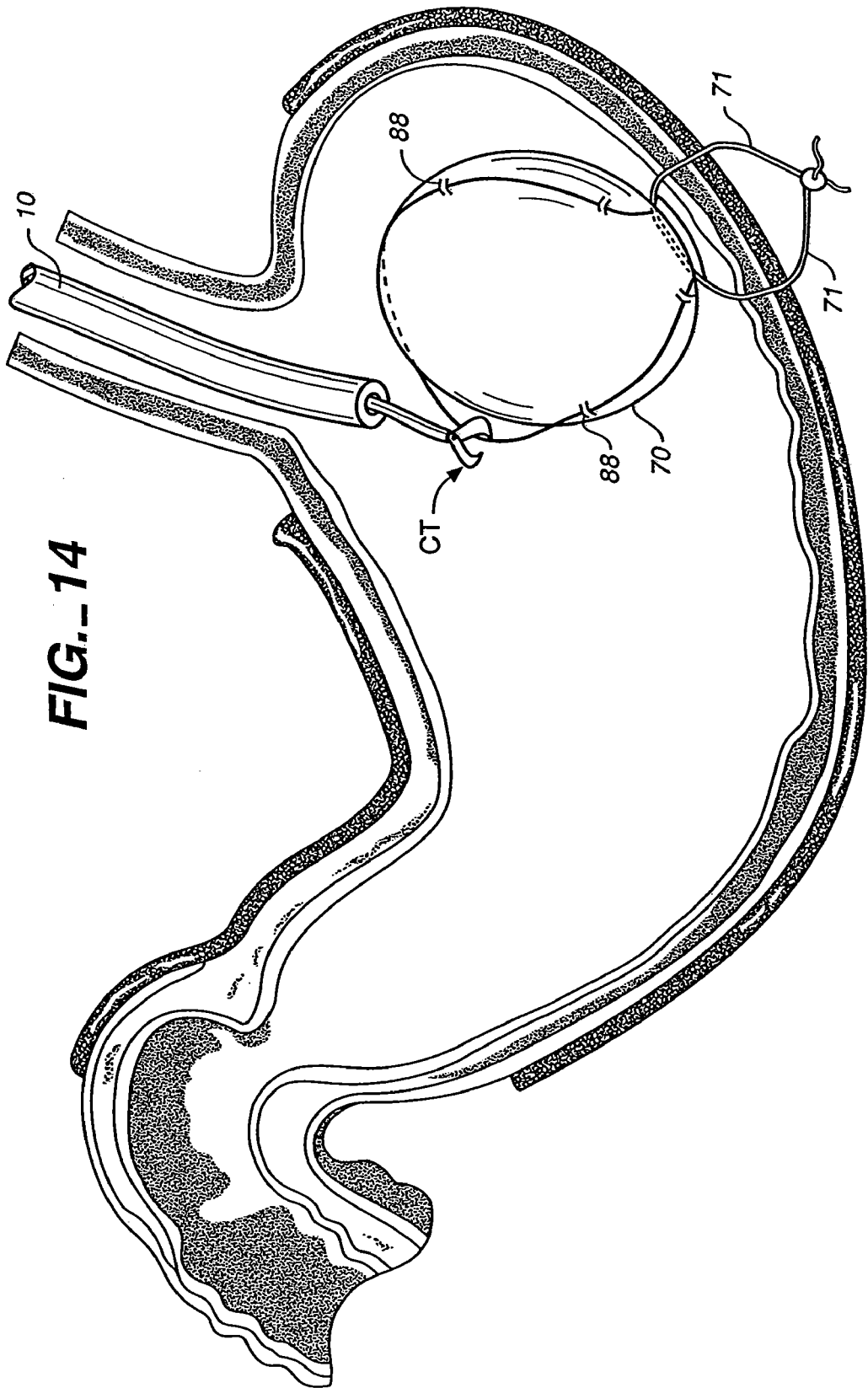
FIG._14

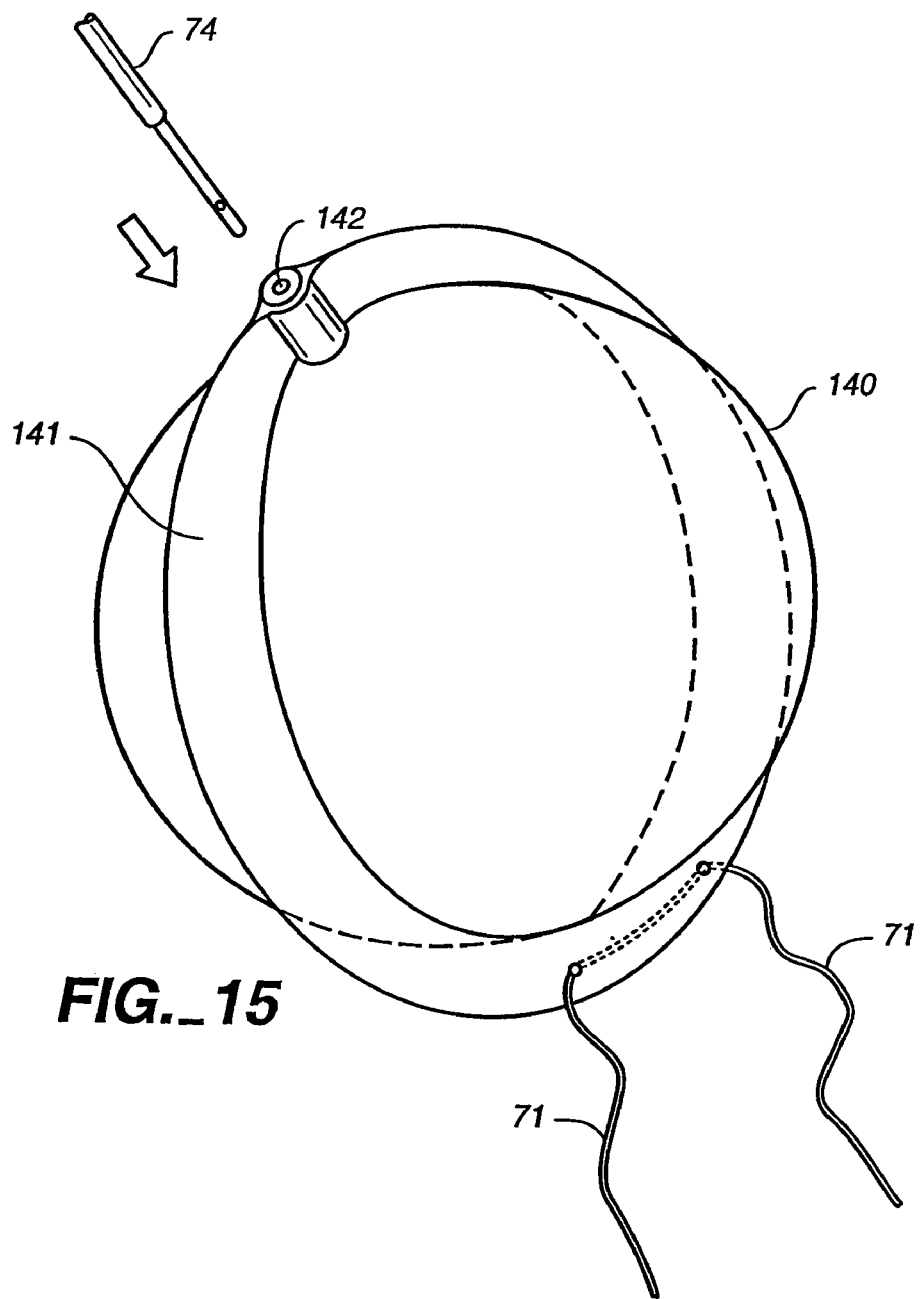
FIG._15

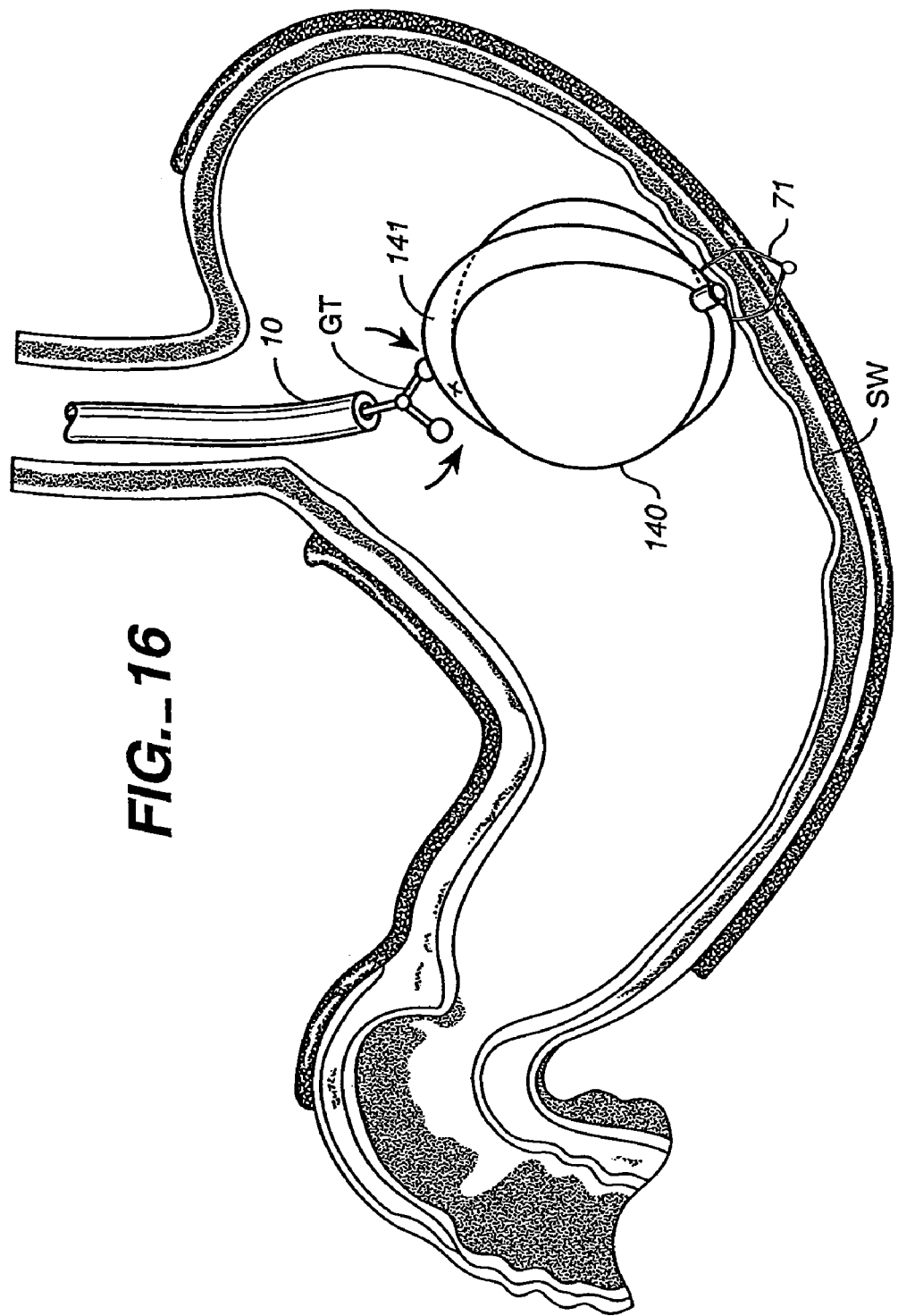
FIG._16

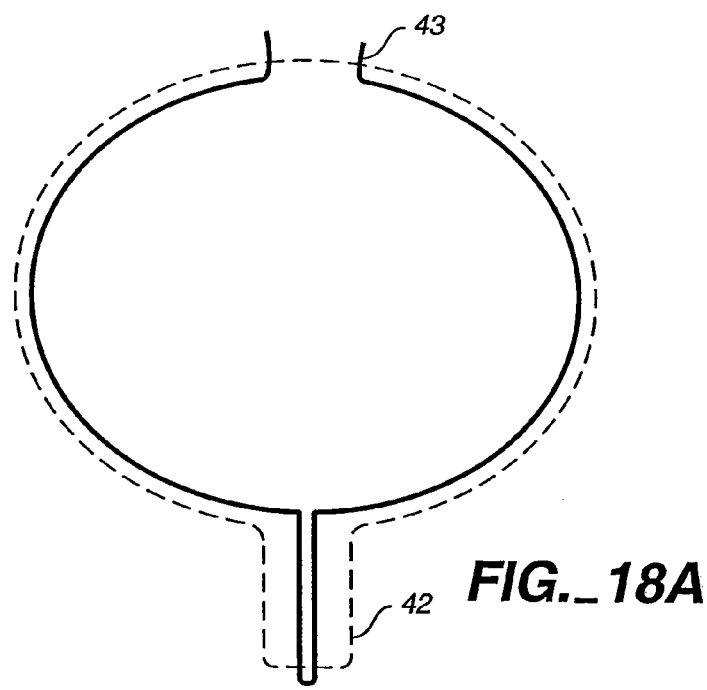
FIG._18A
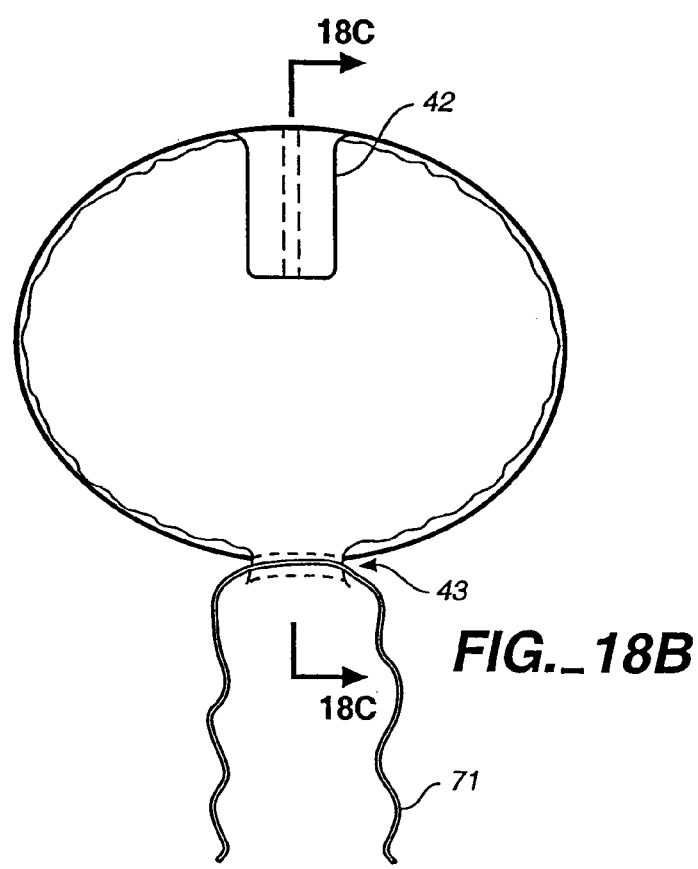
FIG._18B

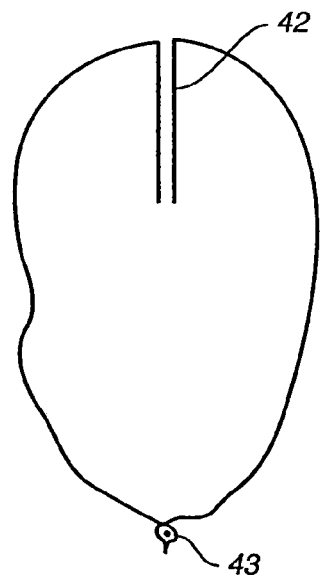
FIG._18C
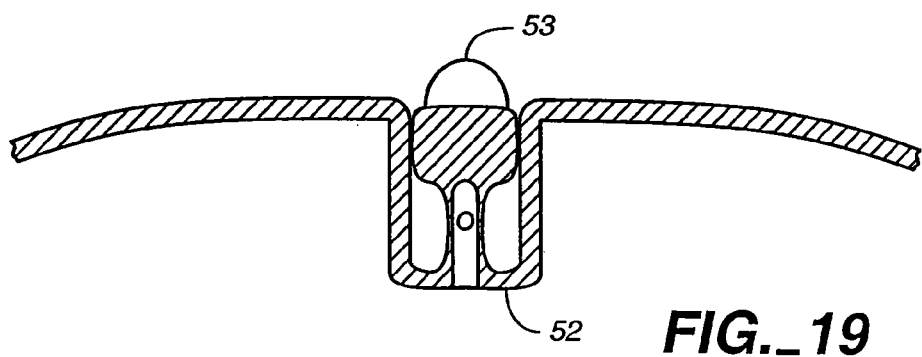
FIG._19

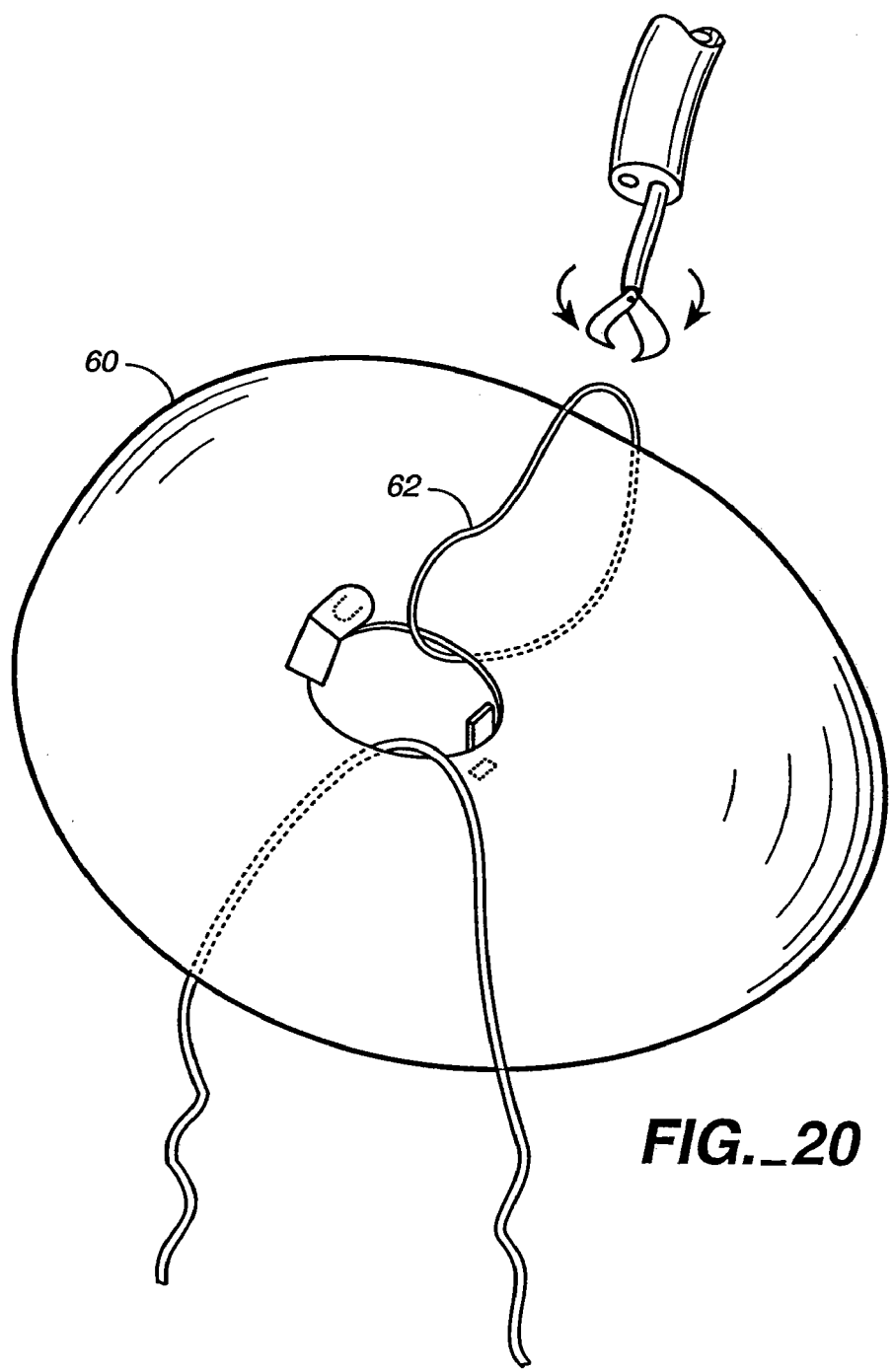
FIG._20

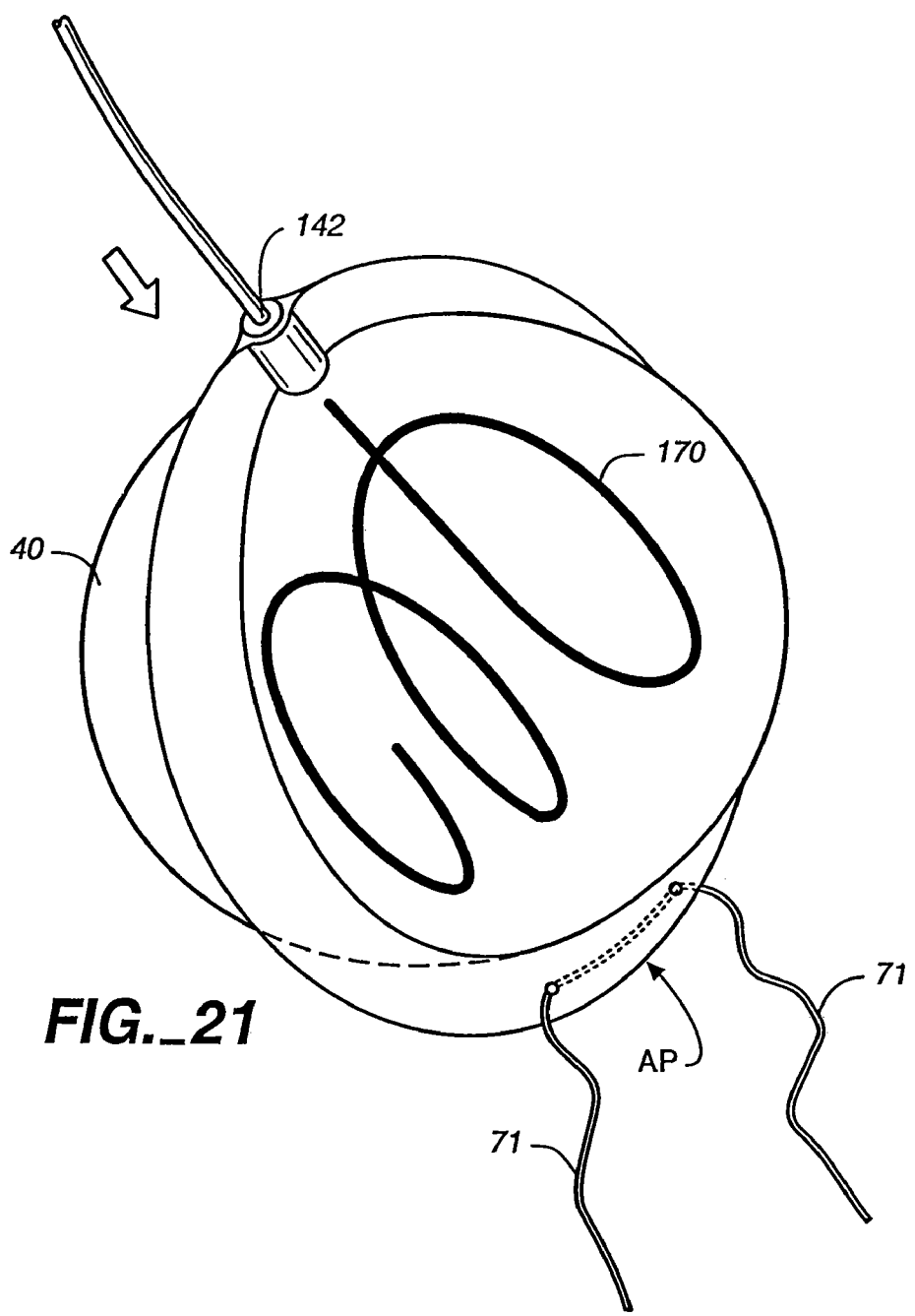
FIG._21

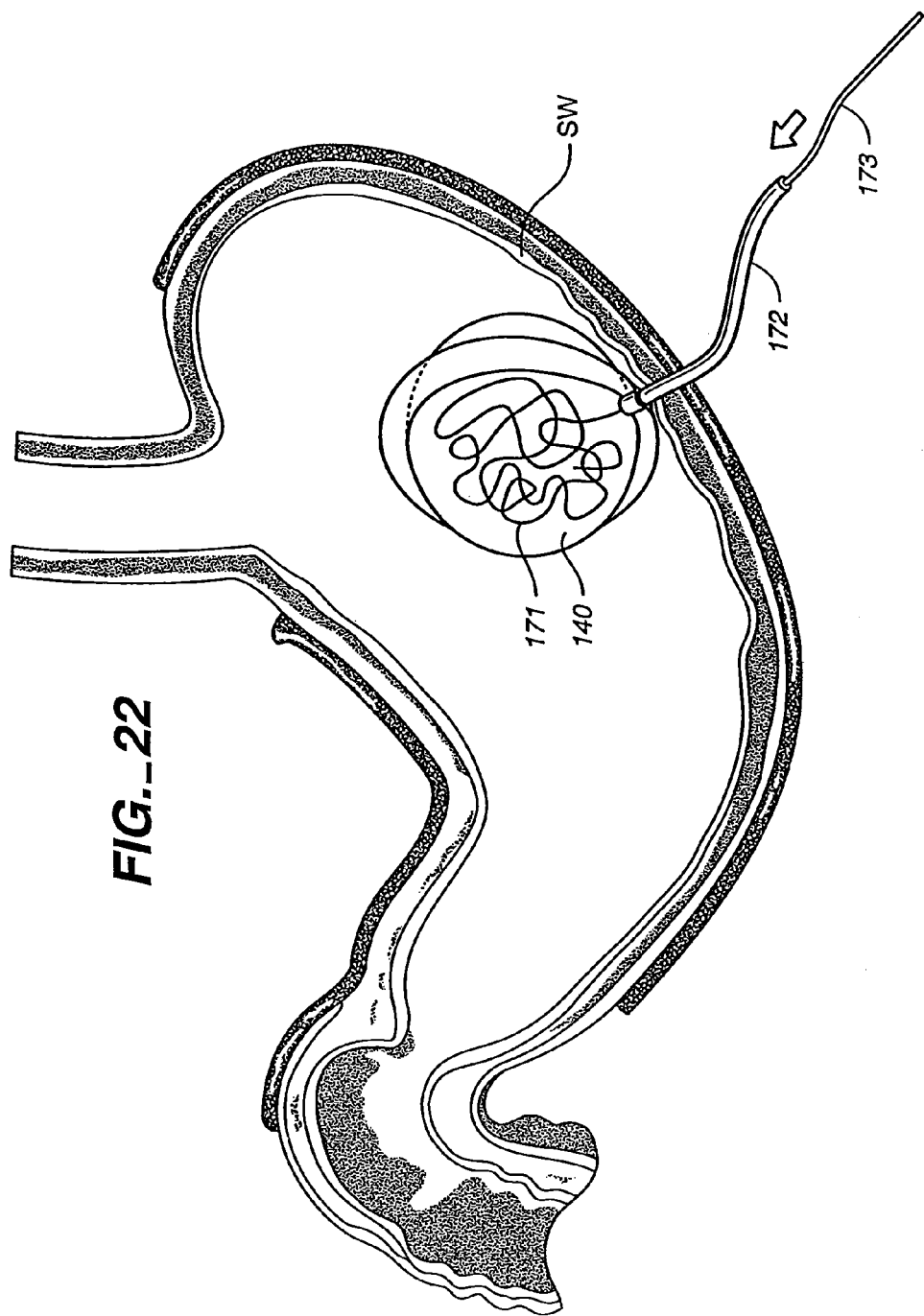
FIG._22

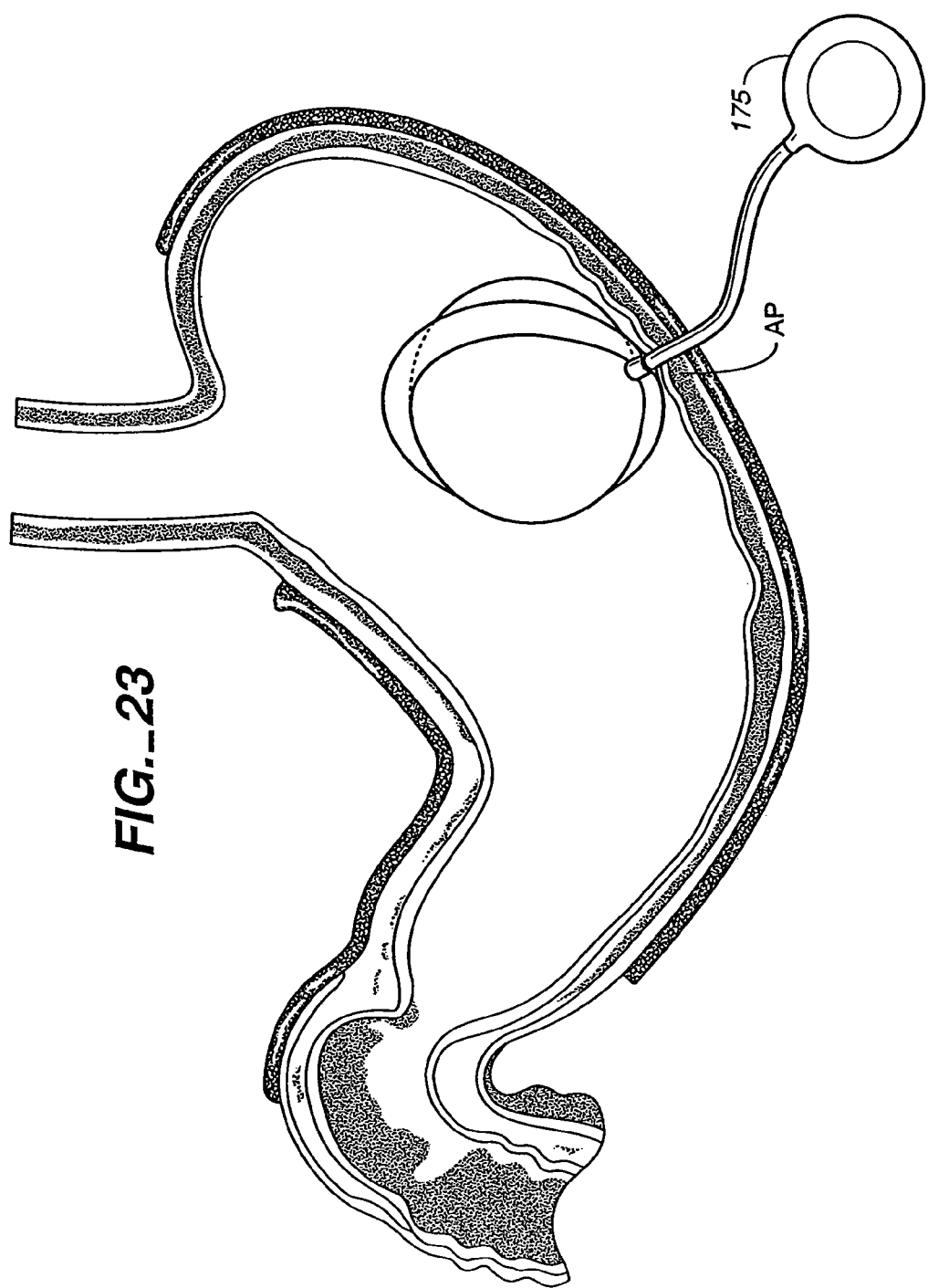
FIG._23

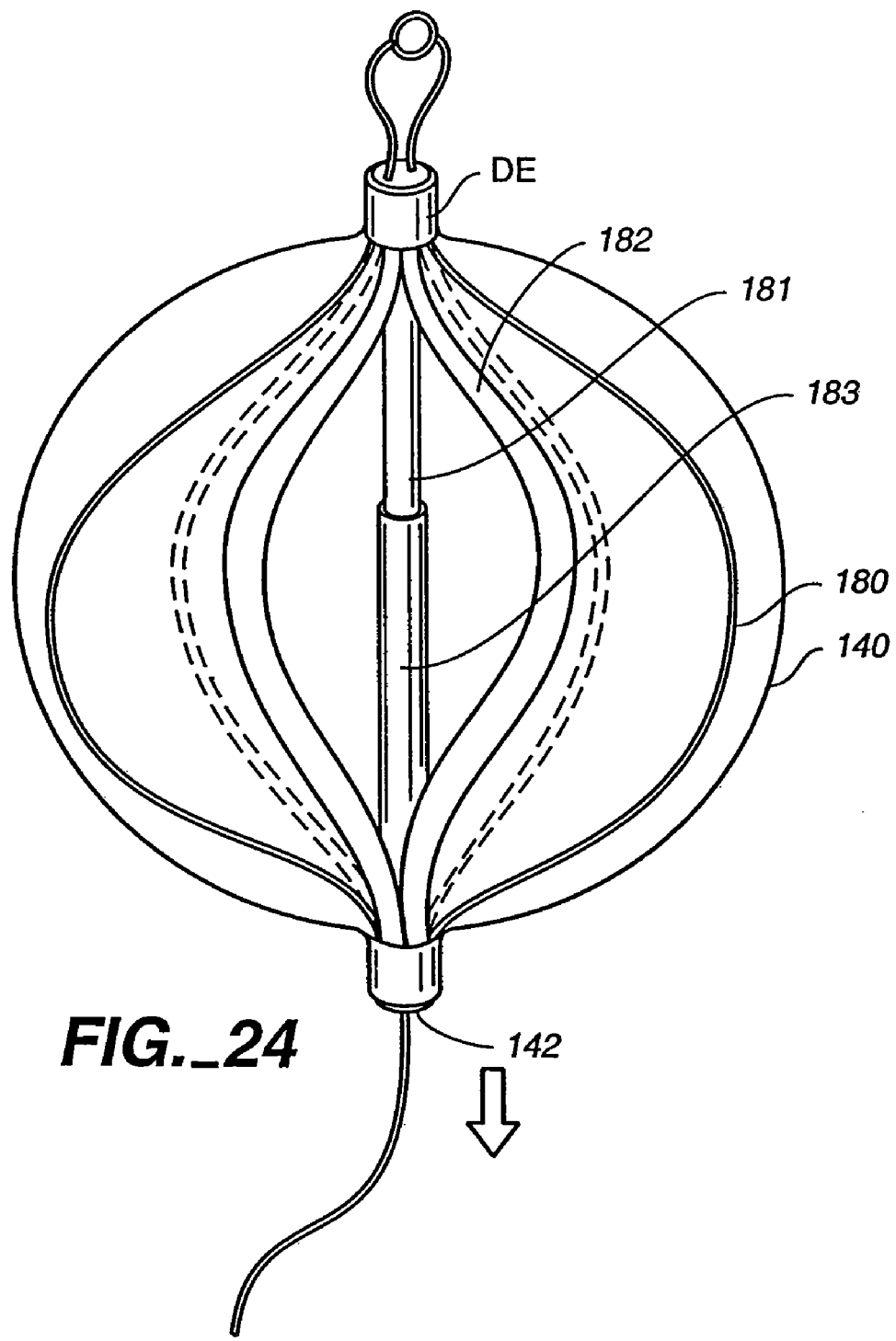
FIG._24

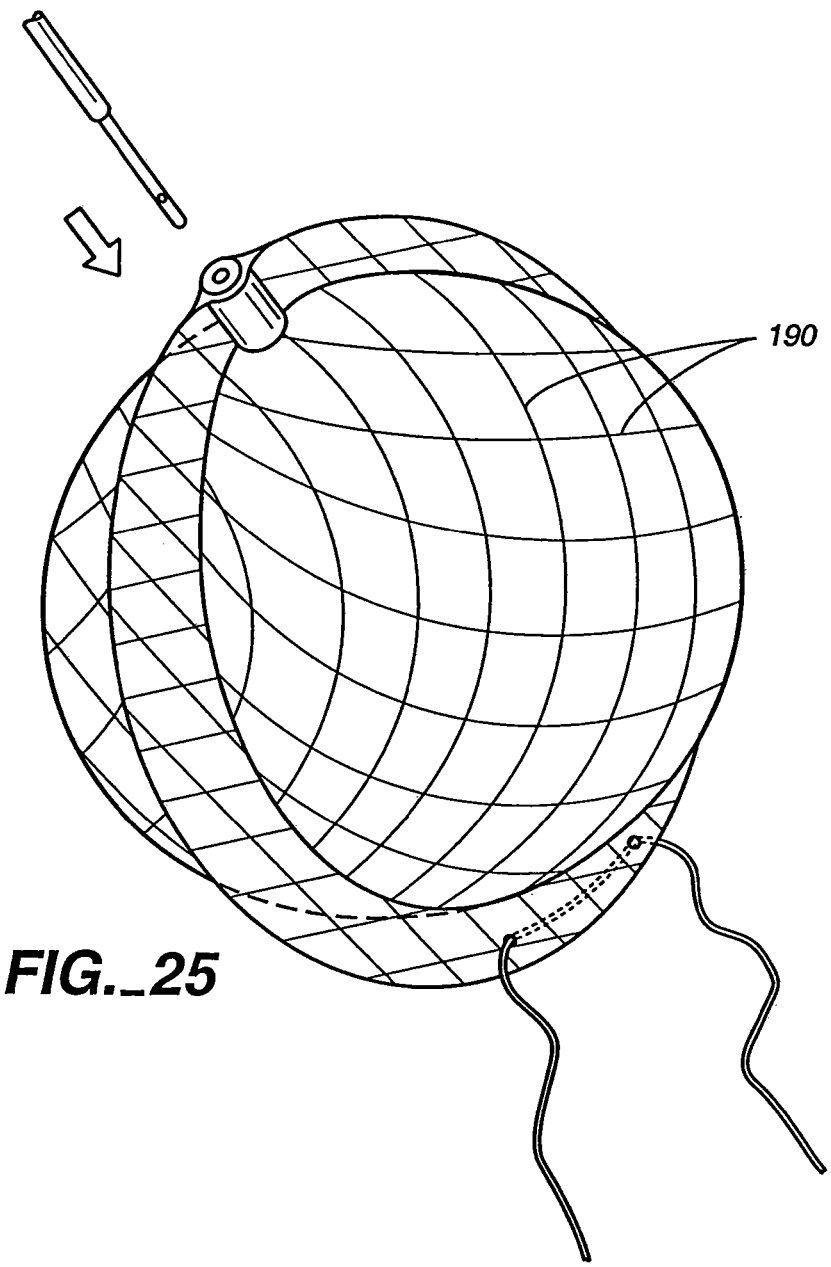
FIG._25

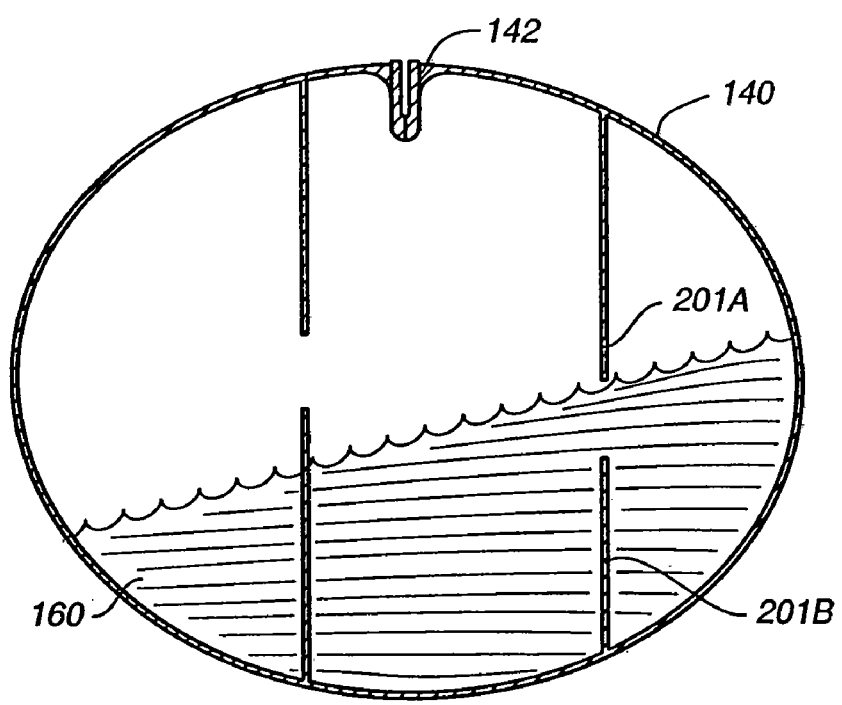
FIG._26

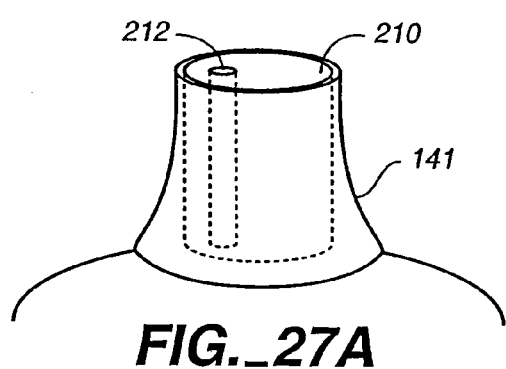
FIG._27A
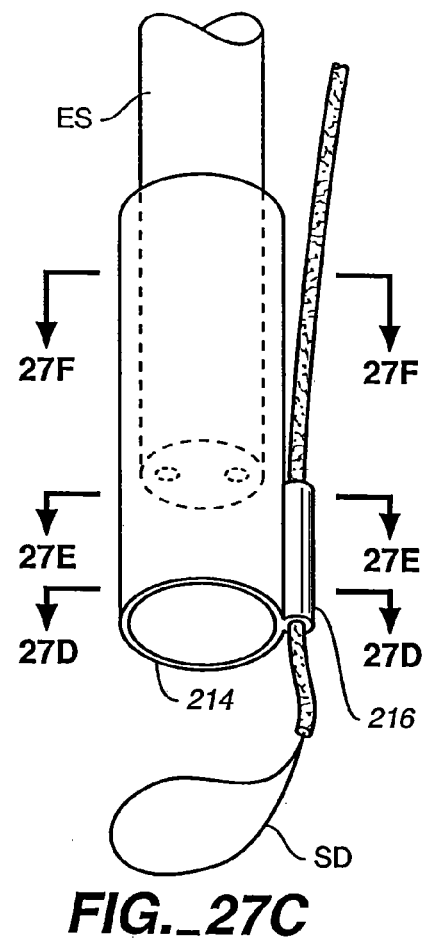
FIG._27C
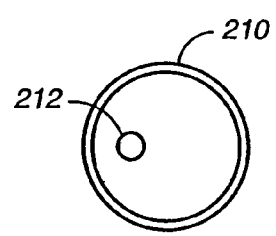
FIG._27B
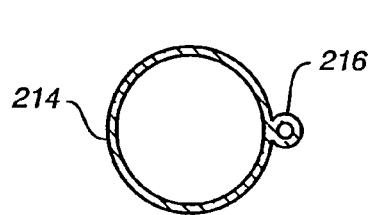
FIG._27D
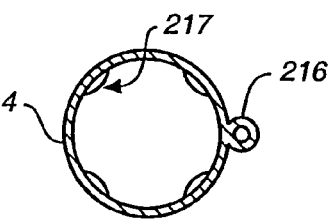
FIG._27E
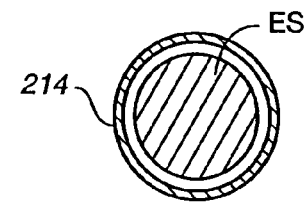
FIG._27F

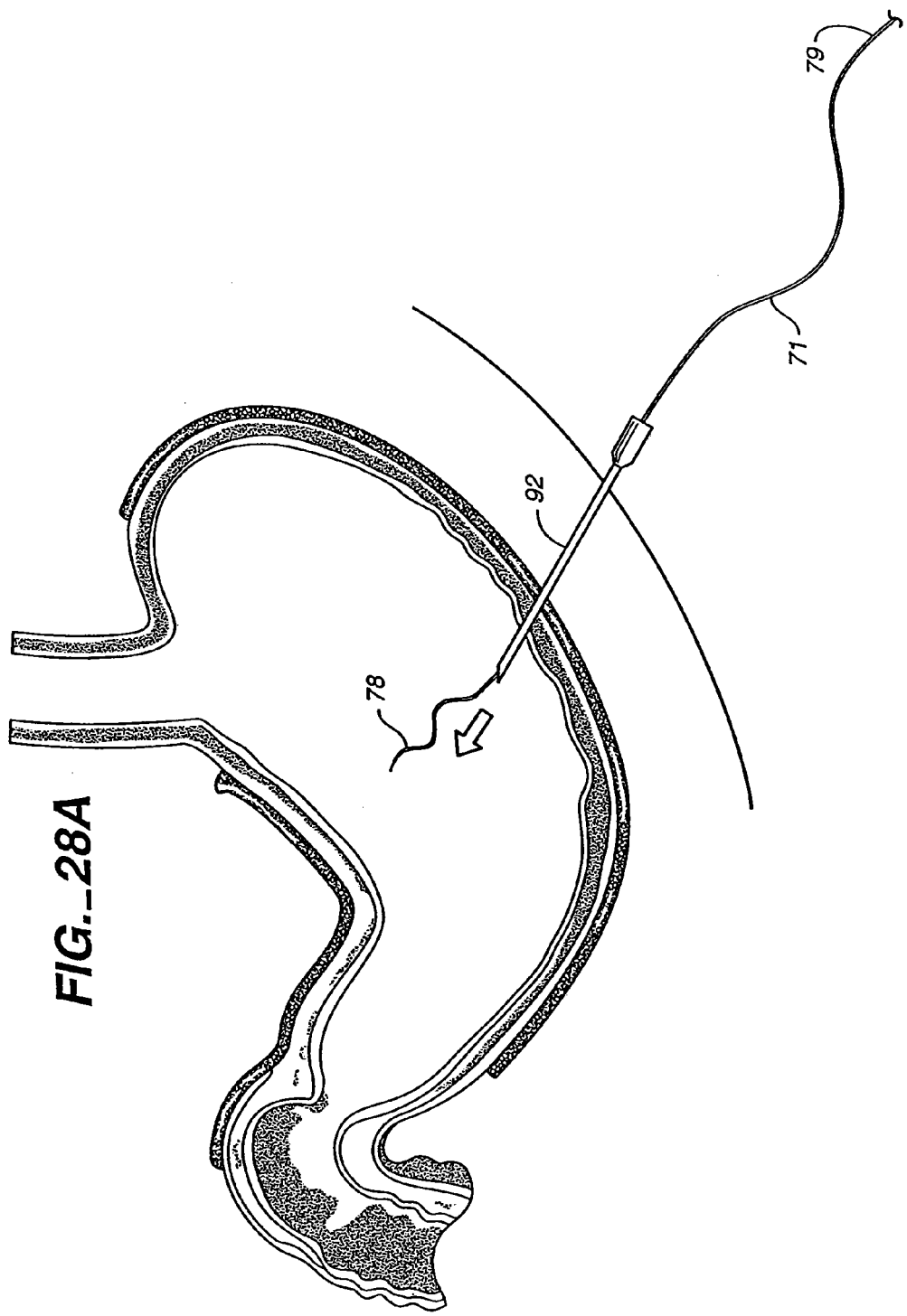
FIG._28A

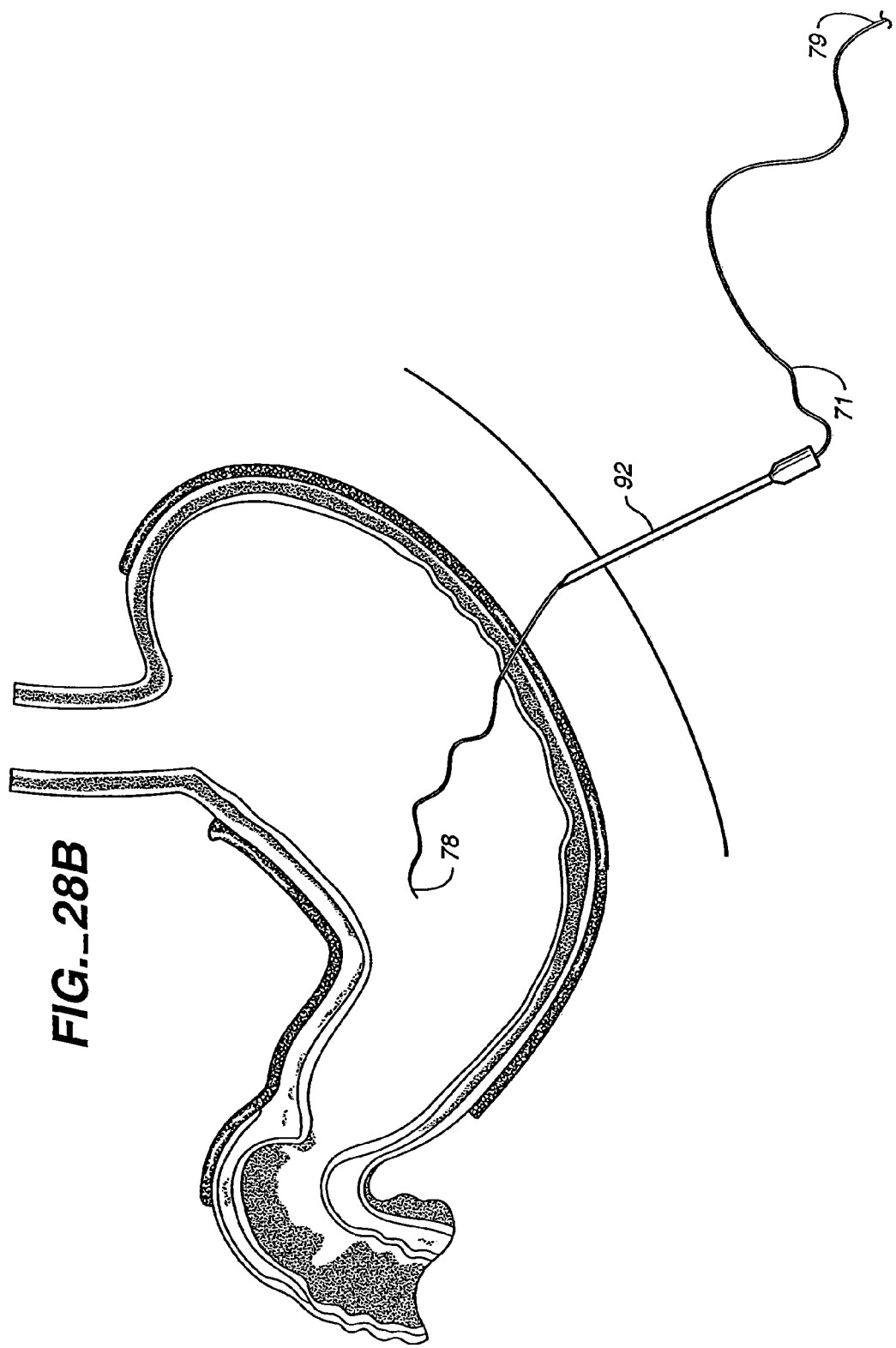
FIG._28B

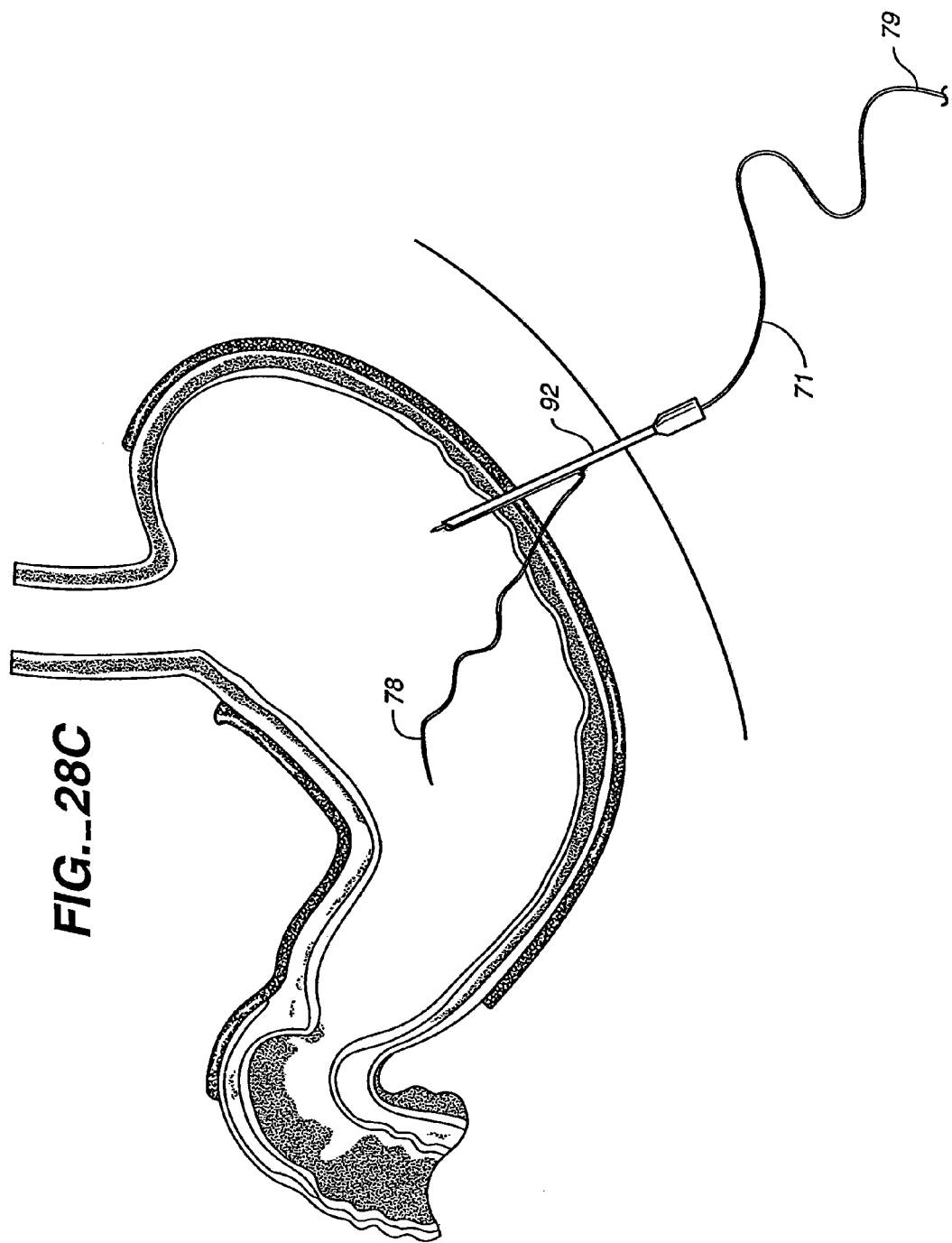

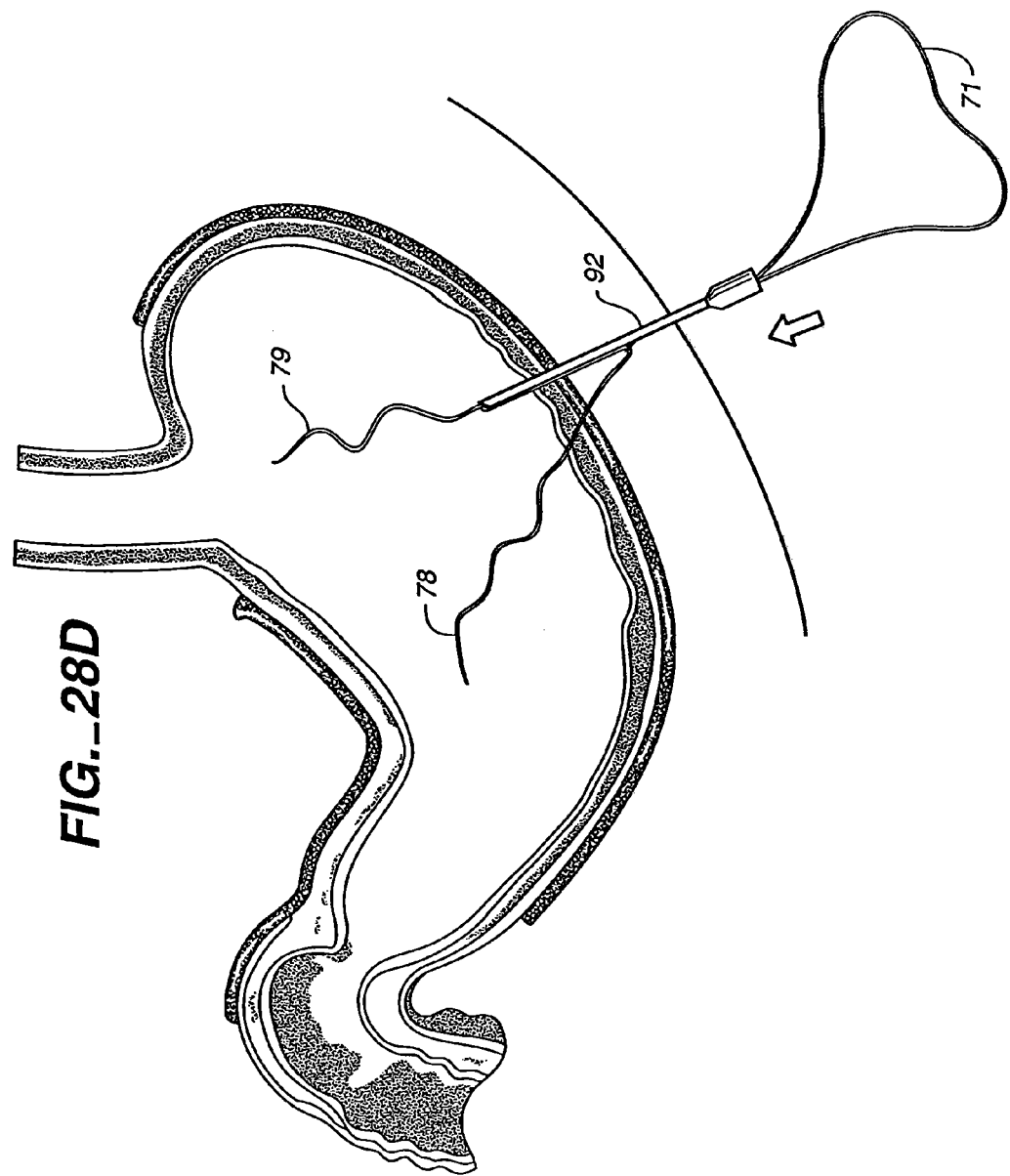
FIG._28D

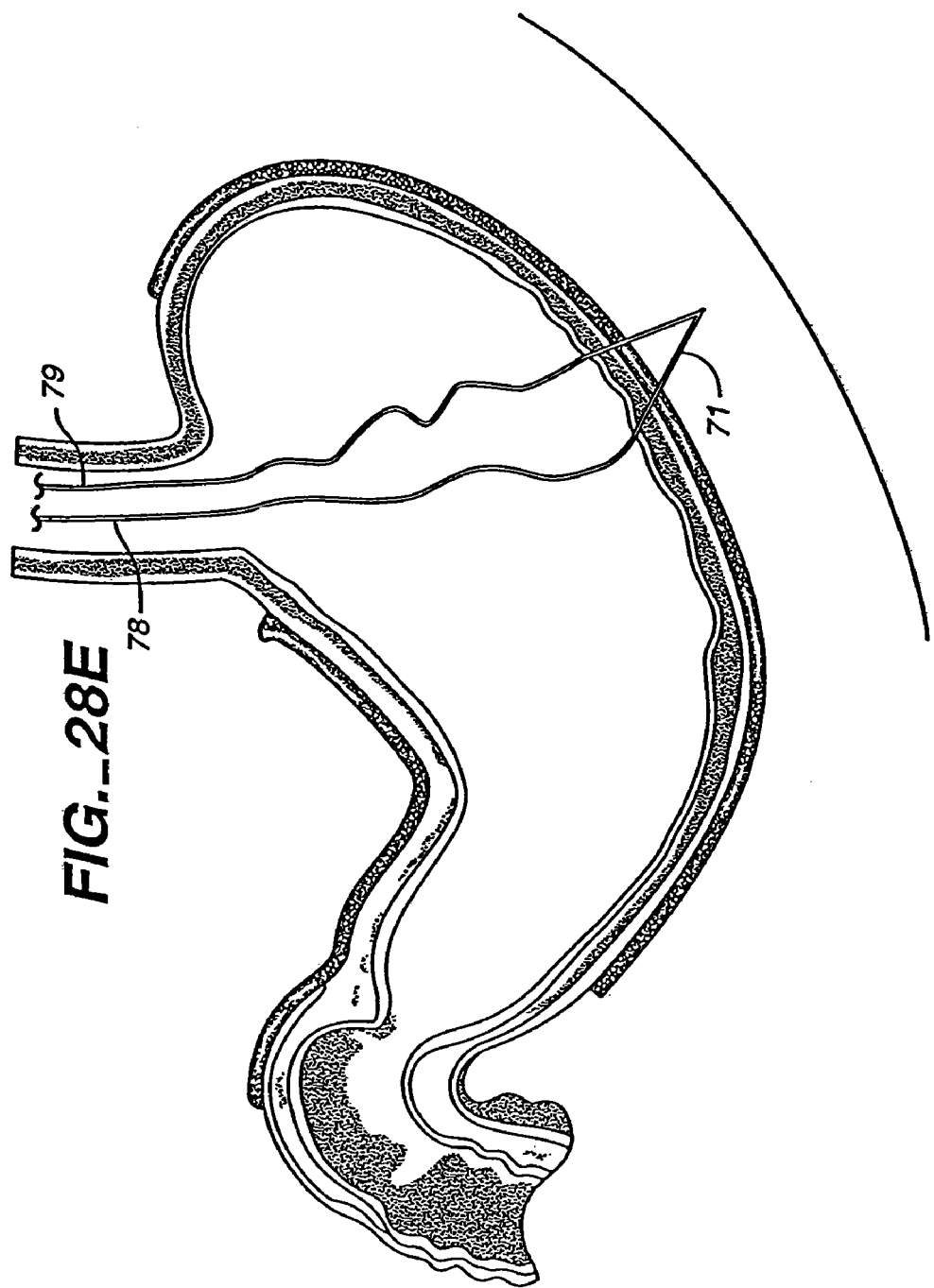

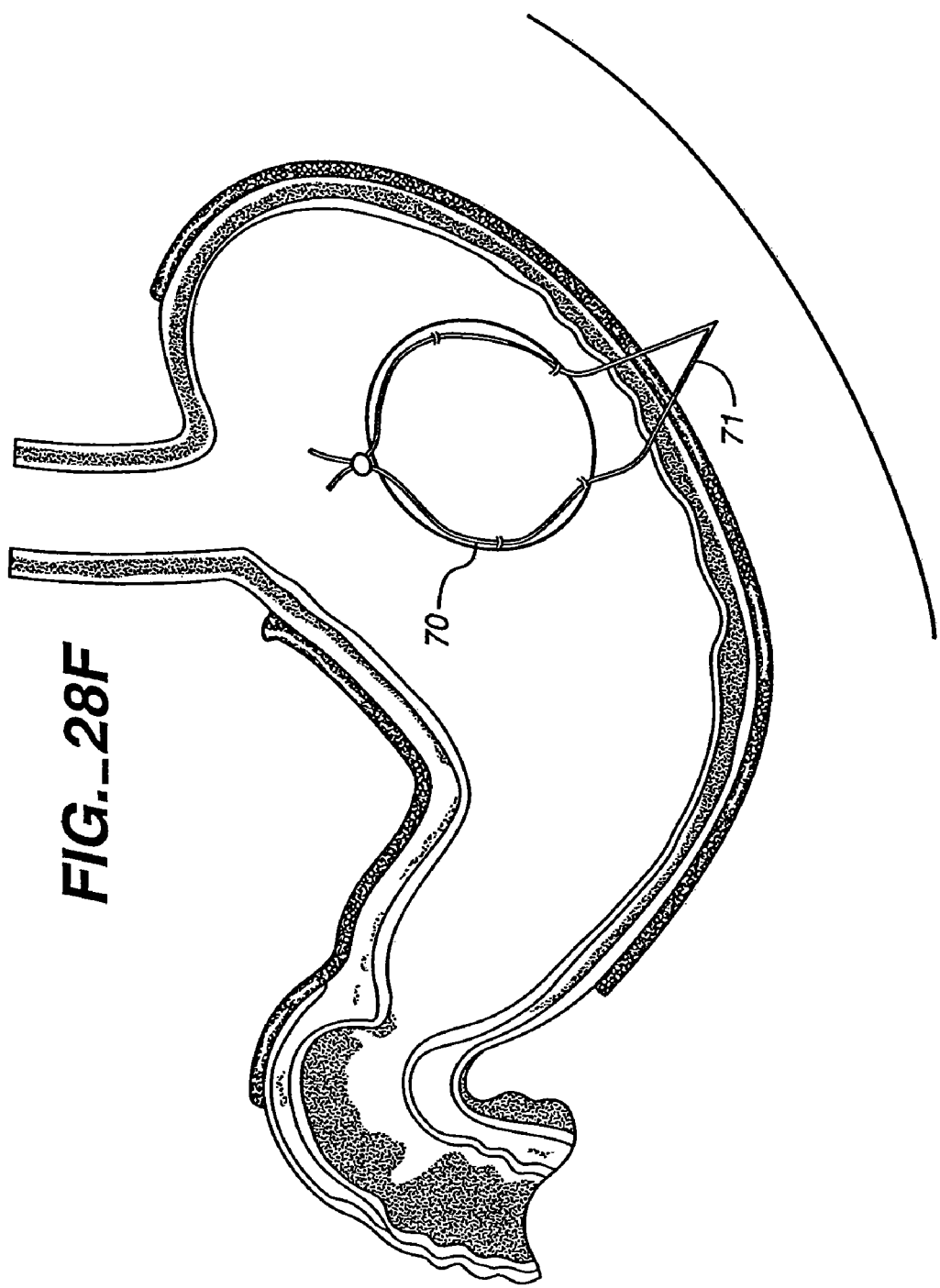
FIG._28F

METHOD AND DEVICE FOR USE IN MINIMALLY INVASIVE PLACEMENT OF INTRAGASTRIC DEVICES

This application claims benefit of priority under 35 U.S.C. §119(e) of U.S. Provisional Application No. 60/245,466, filed Nov. 3, 2000, which is incorporated herein in its entirety.

BACKGROUND OF THE INVENTION

The present invention relates generally to medical apparatus and methods and more particularly to devices and methods for the insertion and securing of expandable devices and the like into a patient's body cavity, such as the stomach, intestine or gastrointestinal track for purposes of taking up space to provide the patient with a feeling of satiety or fullness. These devices may also be removed once they have served their purpose, e.g., the patient has lost the directed or desired amount of weight.

Currently, in cases of severe obesity, patients may undergo several types of surgery either to tie off or staple portions of the large or small intestine or stomach, and/or to bypass portions of the same to reduce the amount of food desired by the patient, and the amount absorbed by the intestinal track. Procedures such as laparoscopic banding, where a device is used to "tie off" or constrict a portion of the stomach, or the placement of intragastric balloons can also achieve these results.

Endoscopic procedures that have been used to assist weight loss have been primarily focused on the placement of a balloon or other space occupying device in the patient's stomach to fill portions of the stomach to provide the patient with the feeling of fullness, thereby reducing food intake. To accomplish these procedures, an endoscope is utilized to guide the balloon through the patient's mouth and down the esophagus to the stomach. Usually these procedures have allowed placement of the device for 6-12 months, and are coupled with counseling and other types of psychological support.

In the case of laparoscopic banding or balloon placement, however, several complications can arise that make these procedures, in their present form, clinically suboptimal. The surgical interventions described above require the patient to submit to an intervention under general anesthesia, and can require large incisions and lengthy recovery time. The less invasive procedures described above, although clinically efficacious in many cases, suffer from complications ranging from deflation of the devices resulting in unsustained weight loss, stomach erosion, bowel obstruction and even death.

Many of these described problems have stemmed from the fact that the devices were not robust enough to sustain long term implantation, and that they were implanted in such a manner as to remain unattached or free-floating within the stomach. Further, due to the caustic nature of stomach acids and other factors, many of the implants deflated and migrated into the intestine, causing bowel obstructions and in some cases death. Also, many devices were not well designed for removal, leading to additional technical difficulties for the clinician.

Additionally, current balloon designs do not allow for the adjustment of balloon size, days or months after initial implantation. This feature would be useful to adjust performance and/or reliability, which may be useful over time.

Because of the limited success of several of these procedures, there remains a need for improved devices and methods for more effective, less invasive, weight loss.

SUMMARY OF THE INVENTION

The present invention meets these and other needs by providing for improved methods and apparatus for implantation and removal of space occupying devices into the gastrointestinal system of a patient, provides for methods and devices for implantation in the stomach of a patient that can be deployed in a minimally invasive manner through clinically established techniques, such as the technique used during a percutaneous endoscopic gastrostomy (PEG) tube placement that includes transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

In one aspect of the invention an expandable device is provided that can be inserted into the stomach of a patient. Its position is maintained within the stomach by anchoring or otherwise fixing the device to the stomach wall of the patient.

In another aspect, the invention provides an expandable device that consists of two portions, an inner portion and an outer portion, the inner portion being able to maintain its shape, regardless of the integrity of the outer portion.

In yet another aspect the invention provides for an expandable balloon device that maintains its expanded shape and desired volume, independent of any small leaks that may develop over time. Furthermore, in the event of leaks, the present invention prevents against migration or contamination to the patient with the contents of the inflated volume.

The present invention also provides for means by which the volume of the space occupying device can be adjusted in-situ, to change the size of the device after implantation.

The present invention to provide tools and methods for removal of the expandable devices, e.g., once the patient has lost the desired amount of weight, or if it is necessary to remove the device for other reasons. The present invention further provides for features that allow the placement and integrity of the space occupying device to be monitored by the physician after implantation using minimally invasive imaging techniques such as x-ray or ultrasound.

More particularly, in an embodiment of the invention an inflatable or otherwise expandable space occupying device is provided that can be delivered or otherwise deployed through the patient's mouth in a transesophageal procedure into the patient's stomach. The device includes an expandable member with one or more fasteners secured thereto. The fasteners are configured such that portions of the fasteners extend at least partially through the patient's stomach wall, thereby maintaining the device within the patient's stomach, but do not extend external to the patient's body. In one embodiment, sutures are used for fastening the device to the patient's stomach wall.

The expandable member may be constructed of a composite material to achieve desirable surface characteristics and is preferably visible under x-ray. In addition, the device of the present invention may have surface features, such as a flange, beads, loops, and/or tabs to facilitate manipulation, deflation and/or removal of the device.

The invention also provides for methods and apparatus for adjusting the volume of the device while it is maintained in the deployed condition.

BRIEF DESCRIPTION OF THE DRAWINGS

FIGS. 1-6 shows a method of placement of the space occupying device of the present invention; with FIG. 1 illustrating an endoscope deployed in the patient's stomach and an external incision typical for performing a gastrostomy procedure; FIG. 2 illustrating a snare introduced through the endoscope of FIG. 1 and snaring a guidewire introduced through a needle cannula; FIGS. 3 and 4 illustrating the guidewires being advanced out of the patient's mouth and being fastened to a space occupying device according to the present invention; FIG. 5 illustrating the device having been pulled into the patient's stomach and an endoscope reinserted; and FIG. 6 illustrating the device anchored with the patient's stomach;

FIG. 7 shows a deployed space occupying device of the present invention, having beads incorporated into an inflated member of the device to aid in grasping and/or deflation of the device;

FIG. 8 shows a method of deflating a space occupying device according to the present invention, illustrating a snare positioned to grasp a bead located on a inflated member of the device;

FIG. 9 shows an expanded view of the bead and snare of FIG. 8, with parts broken away;

FIGS. 10-11 show a space occupying device according to the present invention having tabs adhered to the inflated member of the device to aid in grasping and/or deflating the device, with FIG. 11 illustrating a cross-sectional view with parts broken away of a tab adhered to the inflated member;

FIG. 12 shows a space occupying device according to the present invention having a band extending around the device to aid in grasping and manipulating the device;

FIG. 13 shows a method of removing the space occupying device of FIG. 11, illustrating a snare used to grasp a tab on the device;

FIG. 14 shows a method of releasing a space occupying device according to the present invention from an anchored position in the patient's stomach, illustrating a cutting tool positioned to sever a suture anchoring the device with the patient's stomach;

FIG. 15 shows a space occupying device according to an embodiment of the invention, including a valve and removal flange features;

FIG. 16 shows the device of FIG. 15 deployed in a patient's stomach, with a grasping tool positioned to grasp the flange;

FIGS. 18A-18C show a method of making a space occupying device according to the present invention having another valve configuration, with FIG. 18C illustrating a cross-section of FIG. 18B taken along line 18C-18C;

FIG. 19 shows a space occupying device of the present invention having yet another valve configuration;

FIG. 20 shows a space occupying device according to another embodiment of the present invention having a toroidal configuration and a grasping loop for grasping and manipulating the device;

FIG. 21 shows a space occupying device according to yet another embodiment of the invention, illustrating the device expanded with an expanding element of predetermined shape;

FIG. 22 shows a space occupying device according to yet another embodiment of the invention, illustrating the device expanded with a randomly shaped expanding element according to the present invention deployed in a patient's stomach;

FIG. 23 shows a space occupying device of the present invention connected to a subcutaneous port for modifying the volume of the device in situ;

FIG. 24 shows a space occupying device according to another embodiment of the invention having a deployable expanding element incorporated into the device;

FIG. 25 shows a space occupying device according to the present invention having a radiopaque grid or film placed on a surface of the device;

FIG. 26 illustrates a cross-sectional view space occupying device according to an embodiment of the present invention having internal baffles within the device to control flow and distribution of internal inflation media;

FIG. 27A-27B illustrate a space occupying device according to the present invention having a particular valve and docking construction to allow for in situ modification of the space occupying device volume; with FIGS. 27A and 27B illustrating side and top views of the valve;

FIG. 27C shows an endoscope-docking device assembly, the docking device configured to receive the valve of FIG. 27A;

FIGS. 27D-27F show cross-sectional views of the assembly of FIG. 27C taken along lines 27D-27D, 27E-27E and 27F-27F, respectively; and FIGS. 28A-28E show another method of placement of the space occupying device of the present invention, with FIG. 28A illustrating a needle advanced into a patient's stomach and one end of a piece of suture advanced into the stomach; FIG. 28B illustrating the needle partially withdrawn from the patient; FIGS. 28C and 28D illustrating the needle advanced back into a patient's stomach at a different angle and the opposite end of the piece of suture being advanced into the stomach; FIG. 28E illustrating both ends of the piece of suture advanced out of the patient's stomach and through the esophagus; and FIG. 28F illustrating the device anchored within the stomach by the suture.

DETAILED DESCRIPTION OF THE PREFERRED EMBODIMENTS

The present invention provides for space occupying devices deployable in a patient's stomach, and methods of deployment, manipulation and removal of such devices.

Method of Deployment and Removal

A space occupying device according to the present invention can be deployed into the patient's stomach in a variety of ways, including passing the device through the mouth and down the throat with the aid of an endoscope or like device (transesophageal approach), or by performing procedure similar to a percutaneous gastrostomy procedure and gastric fistula to pass the device through the stomach wall and into the stomach. In a preferred method, a combination of both these approaches is taken, as further described herein. Prior to undergoing this procedure, the patient is preferably sedated to lessen the patient's discomfort, and a local anesthetic may also be applied at the site of the puncture or incision.

Figure 1:
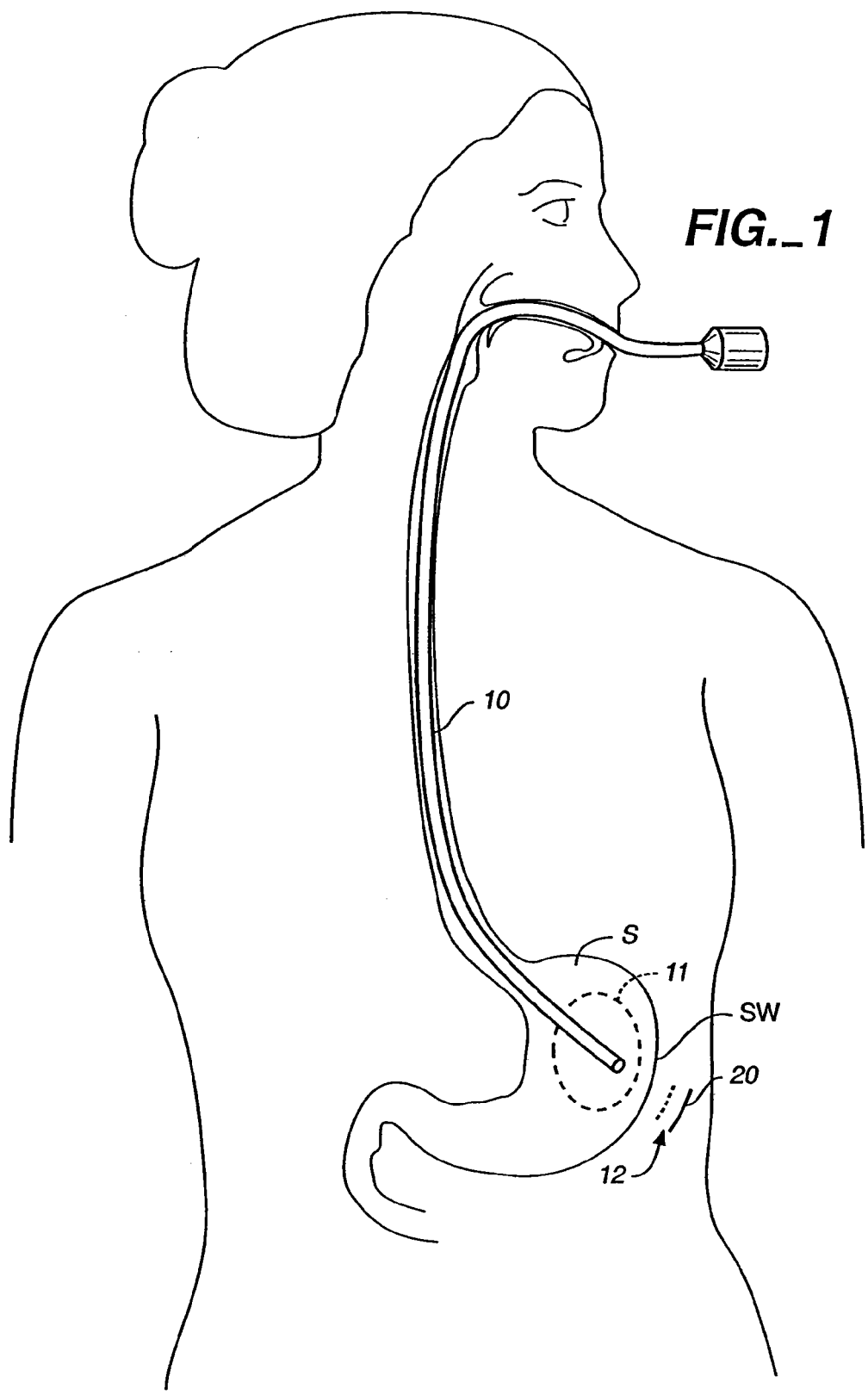

FIGS. 1-6 illustrate in further detail an inventive method of deploying a device of the present invention. FIG. 1 shows a conventional fiberoptic flexible endoscope 10 that has been advanced down a patient's throat and esophagus to an appropriate area 11 within the stomach (S), the distal end of the endoscope being located at or near the wall of the stomach (SW) at the desired location for performing a percutaneous gastrostomy procedure and, ultimately, for anchoring the device of the present invention. The endoscope 10 is then illuminated against the stomach wall (SW) such that the endoscope operator may observe light from the outside of the patient's stomach through the stomach wall (SW) at incision point 12. The location may also be externally palpated and the endoscope operator can observe the resulting indentation via the endoscope. An incision 20 is then made at incision point 12 and extends to the fascia. Incision 20 as shown is approximately 1 cm. It is also possible to make only a puncture to a similar depth without necessitating a scalpel incision, and still deploy the device in accordance with the invention.

Figure 2:
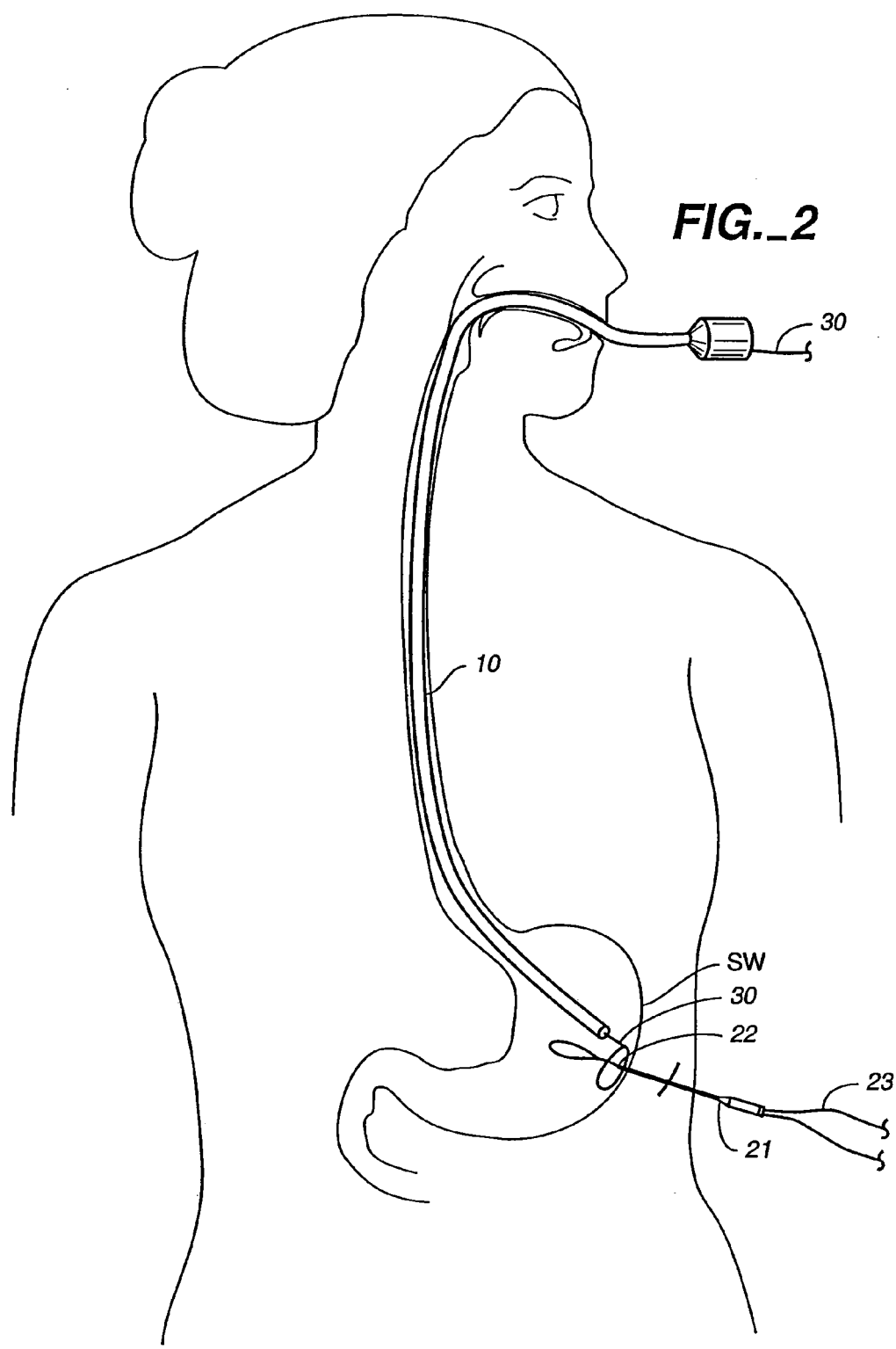
Figure 3:
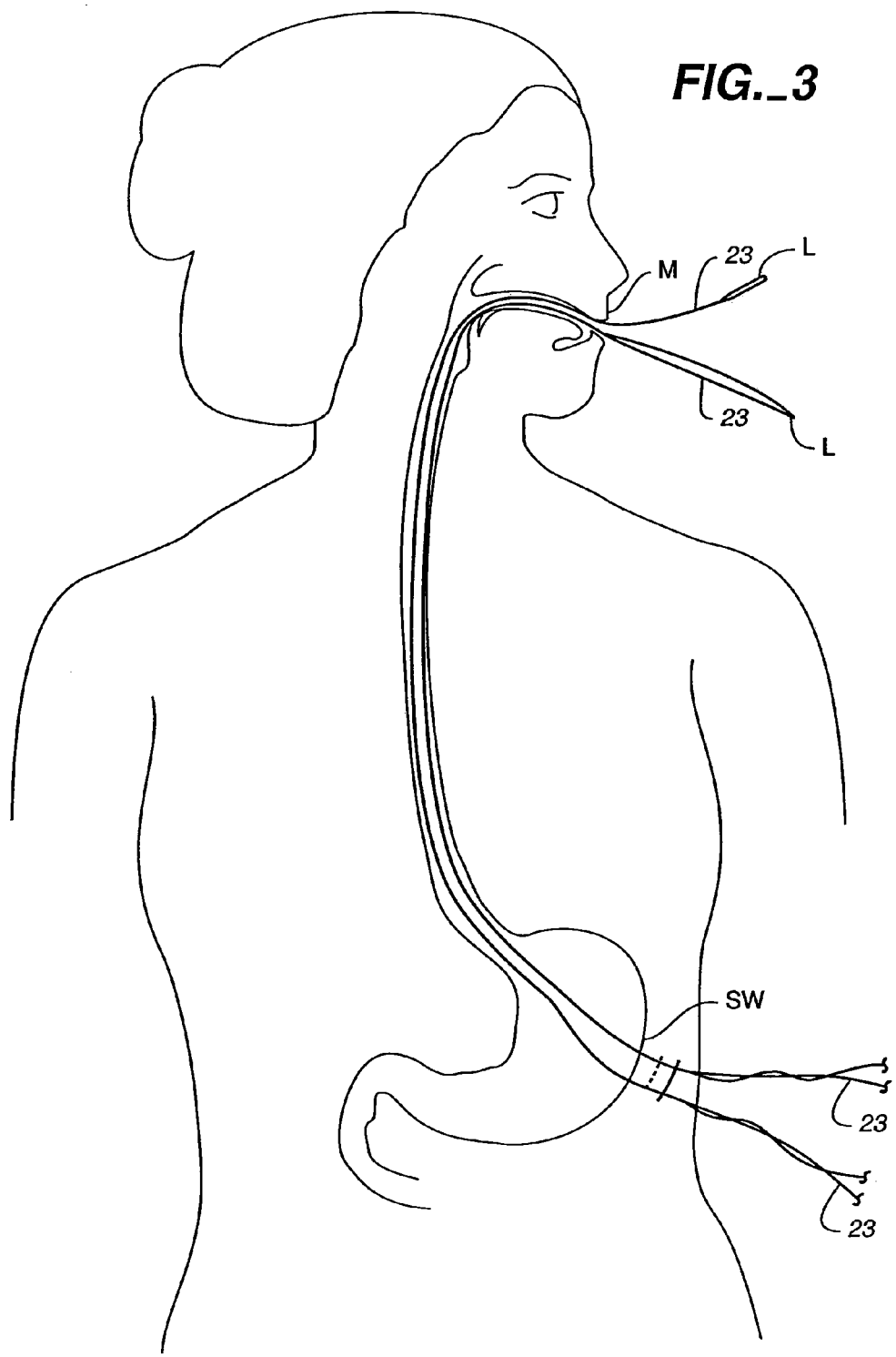

At this point, some of the components typically found in a standard PEG tube set can be employed to assist in the placement of the device of the present invention within the stomach. A typical PEG tube kit, such as the PONSKY "Pull" PEG Kit (C. R. Bard, Inc., Billerica, Mass.), includes, e.g., a needle cannula with stylet, and a guidewire. Various components of this kit can be employed in placement of the device of the present invention as follows: at the point of incision 20, needle cannula 21 with stylet 22 are inserted through the incision, across the anterior stomach wall (SW) and into the stomach (S), as shown in FIG. 2. FIG. 3 further depicts the placement of snare device 30 through the lumen of endoscope 10, while the endoscope is directed toward needle cannula 21.

At this point in the procedure, the physician removes the stylet 22 from needle cannula 21, and inserts guidewire 23 through the lumen of needle cannula 21. The physician then snares guidewire 23 with snare 30, under direct vision via endoscope 10, and tightens the snare to pull on the guidewire. With the snare in the tightened position, endoscope 10 is removed from the patient's esophagus, thereby pulling guidewire 23 out of the stomach, through the esophagus and out the patient's mouth (M). Guidewire 23 is looped at its distal end (L) such that the looped end is positioned outside the patient's mouth (M) once the snaring procedure is complete.

In a preferred method of the present invention, two guidewires are employed and the described guidewire placement and snaring procedure is repeated such that two guidewires 23, 23 are placed through the stomach wall (SW) and the looped ends (L) of each are positioned outside the patient's mouth (M), as depicted in FIG. 3. Also, the two gastrostomies through the stomach wall (SW) are preferably separated by approximately a 1 cm distance.

FIG. 4 shows placement of the space occupying device 70 of the present invention, described in further detail below, over guidewires 23, 23. One or more sutures 71 are attached to space occupying device 70, and are threaded through the loops (L) of guidewires 23, 23. As depicted, space occupying device 70 includes a releasably attached inflator needle 73 and inflator tube 74, including an inflator 75 to inflate or expand the space occupying device 70, once it is placed. Alternatively, the space occupying device can be provided pre-assembled with a sharp pointed needle (not shown), i.e, of a kind typically used for injection of a compound into a patient, which is connected by flexible tubing to a syringe that can be activated to inflate the device. Alternatively, the device can be inflated using a compressed gas system. For example, the inflator tube can be connected to a canister of compressed gas, through a pressure regulator. In this manner the fill rate and balloon pressure can be better controlled. In most cases, a final inflated pressure of about 1-2 psi is desirable.

FIG. 5 illustrates insertion of space occupying device 70 into the patient's stomach by pulling guidewires 23, 23 back through the stomach wall (SW), such that the sutures 71, 71 follow the guidewires 23 down the esophagus into the stomach, and out through the incision 20, or other puncture(s) as applicable. This portion of the procedure may be performed under direct vision by reinserting fiber optic scope 10 and following space occupying device 70 down the esophagus. The sutures can optionally be marked at intervals, e.g., by the use of paint, dye, glue, metallic coatings, and the like, to aid the physician in monitoring the progression of the device deployment. This method provides for facile installation of the device, due to the pulling force transmitted by the guidewires to the device, as opposed to conventional methods of inserting such devices which typically require a pushing force to push the device down the esophagus and into the stomach. Such pushing methods offer less control over the direction of the distal end of the device and can lead to the device getting caught up or snagged in the esophageal tract as it is being inserted. In many cases involving such pushing methods of insertion, sheaths or other similar protective devices are installed onto the device to facilitate navigation of the esophageal tract. In the present method, such sheaths are unnecessary.

Optionally, space occupying device 70 can further include safety leash 76 looped through eyelet 77 secured to the device, as depicted in FIGS. 4 and 5. The leash can be formed of e.g., a suture material. The provision of leash 76 allows for emergency retrieval of the device from the esophagus during deployment of the device. Such retrieval capability is desirable, for example, where a patient begins choking and it becomes necessary to quickly remove the device from the patient's esophagus.

FIG. 6 depicts the process of securing the sutures 71 through the stomach wall (SW), through the peritoneal cavity by tying a subcutaneous knot to anchor the space occupying device against the stomach wall (SW) prior to inflation or expansion. FIG. 6 further shows the anatomy of the stomach wall (SW) and the intervening fascia and adipose layers through which the guidewires 23 are placed. The stomach wall (SW) consists of a muscular layer (including oblique, circular and longitudinal muscle fibers) (MF), a mucosal and sub-mucosal layer ML, and gastric glands and pits on the inside surface (GAG). Fascia layer (FL) surrounds the outside of stomach wall (SW). The knot can then be pushed down under the subcutaneous fat, and can remain at or even within fascia layer (FL). Incision 20 or similar opening puncture is closed by established procedures (e.g. suture, staple or other closure procedure).

Various materials known in the art are suitable for use as sutures, including polypropylene, polyester, and nylon, as well as polytetrafluroethylene (PTFE) suture, such as GORE-TEX® suture. The invention also contemplates the use of other conventional fasteners for securing the device to the stomach wall, including, e.g., endoscopic staplers, cable-ties and the like, and shape memory or superelastic clips that incorporate into tissue, as long as such fasteners are capable of being deployed such that portions of the fasteners extend at least partially through the patient's stomach wall, but they are not required to extend all the way through the patient's abdomen to maintain the device in place, i.e., they do not extend external to the patient's body. By at least partially extending through the stomach wall it is meant that such fasteners extend into at least one of the tissue layers that comprise the stomach wall, including the inside surface (GG), mucosal and sub-mucosal layer (ML), and muscle layer (MF).

It is also within the scope of the present invention to employ a knot marker or other palpable element such as a sterile bead, that will assist during removal of the device. In particular, the physician will be able to palpate the point at which the space occupying device is anchored prior to puncturing the inflated device or otherwise excising the knot location. This palpable element may also be used to confirm the location of the anchor physically without x-ray, to make sure the device has not migrated during the therapeutic life of the space occupying device. The marker can be, for example, a surgical pledget or button through which the sutures are tied off. Knot markers can include two or more suture holes radially spaced around a center deflation hole. The sutures can be passed through the suture holes and tied off. The deflation hole can aid in a methods of deflating the device, as further described herein. These knot markers may also act as strain relief mechanisms as further discussed below.

Once anchored, space occupying device 70 is then inflated, as seen in FIG. 7, and inflation needle and inflator tube 74 are then withdrawn from the patient's stomach out the patient's mouth, leaving the space occupying device 70, anchored to the stomach wall (SW). The patient can then be monitored over time to confirm weight loss. The area of the stomach to which the space occupying device is secured may be varied depending on the placement that is most advantageous to the patient's weight loss, or feeling of satiety, relating to achieving weight loss. In some cases, it is preferable to place the device at the fundus of the stomach, close to the esophageal orifice.

Once the desired weight loss has been achieved, it is desirable that space occupying device 70 be easily collapsed and removed from the patient's stomach. During the removal procedure, a standard endoscope 10, is deployed down the patient's esophagus to view space occupying device 70 directly. In addition to the scope, a scissor tool or grasper 110, is deployed therewith to grasp or otherwise cut the space occupying device to steady it and/or deflate it in preparation for removal. The grasping of the space occupying device 70 can be further facilitated by certain surface characteristics of the device as further described herein.

One advantageous method of deflating the device involves inserting a needle or other sharp object directly into the stomach from the stomach exterior at or near the anchor location of the device. Using the external scar of the gastrostomy procedure as a guide, the general location of the anchor point of device can be fairly well approximated. In the case of, e.g., a tie-off button, the button can be palpated and the center of the button, which generally corresponds to the anchor point, can be readily ascertained. The deflation needle can then be inserted through the center of the button to pierce and deflate the balloon.

Once space occupying device 70 has been deflated or otherwise contracted, a percutaneous stick or incision can be made externally through the abdominal wall (AW) to facilitate the release of the knot secured earlier in the procedure during anchoring. After the anchoring mechanism has been released and space occupying device 70 has been deflated or otherwise contracted, the entire device can be removed from the patient's stomach using, e.g., an endoscope and grasping device. The skin puncture or incision is then closed.

Alternatively, one or more steps of deflating the balloon, cutting or otherwise severing the anchoring sutures, and removing the device can be accomplished by means of a snare and various beads or tabs or other like protrusions attached to or incorporated directly into the balloon itself. FIG. 8 depicts device 70 having deflation bead 81 extending from the surface of the device, with snare 90 positioned to grasp the bead. As seen in FIG. 9, the bead is secured to loop 82, formed of a suture material, which itself spans the wall of the inflatable member. When the bead is grasped by the snare and pulled away from the balloon, loop 82 is also pulled away from the balloon. This causes a tear or a rip in the inflatable member at the site of insertion of the loop, resulting in deflation of the balloon.

Another method for deflating the device is illustrated in FIG. 19, which depicts a balloon member having a retractable deflation valve 52 with suture loop 53 attached to top portion of the valve and extending from the balloon surface. A valve of this configuration is in a sealed or closed position when the valve body is pushed down and seated into a retracted position within the balloon. Typically, the balloon will be inflated by other means. When the deflation valve body is pulled upward, by, for example, pulling on suture loop 53, the valve opens. An grasping tool can be used to grasp and pull suture loop 53, thus opening the valve and deflating the balloon.

The device of the present invention can also include beads and/or suture loops and/or tabs that are attached to or are integral with balloon member, and which can be used to remove the device from the patient's stomach. For example, FIG. 7 illustrates device 70 having grasping beads 85 that are secured to and extend from the balloon surface, and FIG. 11 shows a device having tabs 91 secured to the balloon surface. As depicted in FIG. 13, snare 90 can be used to grasp tab 91 and can similarly be used to grasp beads 85. Once the balloon is deflated and the sutures cut or otherwise severed, the snare can be used to pull the device from the patient's stomach. As depicted in FIG. 13, device 70 is in a deflated condition, but the grasping of tab 91, or a bead or suture loop, can also be accomplished when the device is in the inflated condition.

Another method for removing the device is shown in FIG. 14, which illustrates a device where suture 71 extends around the circumference of the balloon, and is threaded through guides 88 to retain the position of the suture relative to the balloon. A cutting tool (CT) is deployed through endoscope 10 to cut or sever the suture. With the suture severed, the device is then freed for removal from its anchored position.

FIGS. 28A-28F illustrate another method according to the present invention of placing a space-occupying device that does not require a percutaneous endoscopic gastrostomy or like procedure. Rather, as shown in FIG. 28A, needle 92 is positioned externally of the patient's stomach and inserted at a first angle through the patient's stomach wall and into the stomach itself. Suture 71 is then fed through the needle until a first end portion 78 of the suture is deposited into the stomach. The needle is then partially withdrawn from the stomach such that the needle tip either remains within the stomach wall itself or at least remains within the peritoneal cavity is not withdrawn into the external layer of the abdominal wall, as seen in FIG. 28B. The needle is then advanced at a second angle into the stomach and the opposite end portion 79 of the suture is advanced through the needle and deposited into the patient's stomach, as shown in FIGS. 28C-28D. At this point the needle can be completely withdrawn, and the two suture ends can be grasped by a grasping tool and pulled out through the patient's esophagus, throat and mouth, as seen in FIG. 28E and much as described above with respect to guidewires 23.

A space occupying device is then secured to one end of the suture (not shown) and by then pulling on the opposite end of the suture the device can be pulled through the patient's mouth, throat and esophagus for placement in the stomach. It is desirable to include a guide (not shown) on the device through with the opposite end of the suture can be threaded. Once the device is placed the suture can then be secured to the guide, such as by tying off the suture to the guide, or by other known means, in order to anchor the device in place, as shown in FIG. 28F.

This method is advantageous in that it offers an even more minimally invasive approach than using a percutaneous endoscopic gastrostomy technique, as there is only a single puncture site required. In a variation of the method, guiding suture 69 is also introduced into the patient's stomach using a needle, and a portion of this guiding suture is likewise pulled via an endoscope out of the patient's mouth and secured to the device. By exerting a pulling force on the portion of the guiding suture remaining external to the patient's abdomen, the device can be pulled into position and tied-down. The guiding wire can be cut or otherwise released from the device.

The device can also be placed using a method that relies on a predominantly endoscopic approach without requiring a percutaneous endoscopic gastrostomy or even accessing the stomach from the patient's exterior. This method employs an endoscopic suturing device, such as the ENDOCINCH™ endoscopic suturing device (C. R. Bard, Inc., Billerica, Mass.). The device includes a capsule and a needle that is advanced via an endoscope down a patient's throat to a desired location within the patient's stomach. The needle includes loaded suture with a suture tag. The device includes a capsule having an opening that is placed against the stomach tissue, and a vacuum is applied to bring a fold of tissue into a chamber of the capsule. The needle is then advanced through the fold, deploying the suture and suture tag, which is captured in the end cap of the capsule. The device is then withdrawn, leaving suture passing through the stomach tissue and two free ends of the suture running out of the patient's mouth. The device of the invention can then be attached and/or threaded onto the suture ends and advanced into the patient's stomach. For example, one end can be tied to device and the other end used to pull the device down the patient's esophagus, as described above, and then tied off. Alternatively, both ends of the sutures can be threaded through guides on the device, and the device can be pushed down the patient's esophagus and into place using a delivery catheter or sheath or the like. In either method, the sutures can be tied down, securing the device in place, using knot pushers known in the art, such as, e.g., those described in U.S. Pat. Nos. 5,391,176 and 5,527,323, each of which is incorporated herein in its entirety. Alternatively, the endoscopic suturing steps can be repeated to provide multiple anchoring sites in the stomach tissue for anchoring the device.

Expandable Devices

Reference has been made throughout the previous section, to a space occupying device 70. The following descriptions are intended to add detail and further description to the composition and structure of such space occupying device and other attendant features. The space occupying device contemplated by the present invention will preferably have the characteristics of a low profile insertion diameter, capable of expanding to a larger diameter to fill the stomach with the required volume to achieve the feeling of fullness, or satiety, in the subject patient. There are various embodiments that fulfill these requirements, and that are the subject of the present invention.

As described, one embodiment of the space occupying device is an expandable device comprising an inflatable balloon as depicted in FIG. 15. Outer member 140 may be formed of a polymeric material such as silicone, polyethylene, vinyl, polyurethane, urethane or the like, or a material such as mylar, aluminized mylar, neoprene, non-polymeric or thin walled metal materials or other similar materials. Outer member 140 is formed of two sheets of material that are laminated together leaving a seam or flange 141.

Flange 141 may be used as a mechanism to assist in removal of the space occupying device as shown in FIG. 16. For removal, endoscope 10 is inserted using the transesophageal approach into the stomach to the proximity of the implanted space occupying device, through which a grasping tool (GT), such as a laparoscopic grasper or biopsy tool such that when actuated, can engage the flange 141 such that once the space occupying device is deflated and any anchoring released, the grasping tool (GT) can be pulled along with the scope thereby extracting the space occupying device.

While the space occupying device is shown with the flange portion external of the sphere, it is also contemplated by the present invention that the flange may extend inwardly of the space occupying device, thereby providing a smooth exterior, or the space occupying device may be formed as to have no seam whatsoever, but merely an orifice for the valve mechanism. In addition, it is also contemplated by the present invention that the flange may be asymmetric, i.e. only present around a partial circumference of the space occupying device to facilitate grasping, but to minimize any erosive effect on the portion of the stomach wall (SW) with which the space occupying device comes in contact once secured at the anchoring point (AP). For example, the durometer or material at the anchoring point (AP) may be softer than that used in the other portions of the space occupying device.

In a preferred embodiment, the balloon is formed of a urethane interior and a silicone exterior. The urethane provides a durability to the balloon for resisting undesirable rupture or leakage and the silicone exterior provides for a smoothness, and conformability to avoid unnecessary trauma or irritation to the stomach lining.

In another embodiment of the balloon, the balloon is formed of a composite of silicone, aluminized polyester film, and polyethylene. In this embodiment, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space occupying device can be rotated as the silicone cures, to allow for a more consistent coating to form.

A variety of sizes and shapes of the balloon are contemplated by the invention, and it is to be appreciated that one skilled in the art would be competent to choose a particular shape and size according to the particular application. The balloon can be, for example, spherical or ellipsoidal or another suitable shape. In the case of an ellipsoidal balloon, a preferred method of anchoring such a balloon is along the longer axis of the balloon. Balloon volumes can vary, but a typical volume is approximately 500 cubic centimeters (cc).

The deflation, grasping, and suture beads described above can all be formed of a variety of materials, including metals or plastics, provided they are inert, biocompatible, and capable of withstanding acidic stomach conditions, and exposure to consumed food and liquids. It is desirable that the beads be formed of a moldable plastic, such as polycarbonate, polyethylene, or polypropylene. The beads can also be formed of a radiopaque material, such as a metal, or a plastic containing radiopaque material, e.g., barium sulfate ($BaSO_4$), as an aid in monitoring placement of the device as further described herein.

For deflation beads, the beads can be located on and secured to the balloon wall as shown in detail in FIG. 9, using loop 82. The loop can be, for example, formed of a piece of suture passed through the balloon wall and tied off, and then again passed through a through hole in the bead and again tied off or otherwise secured. Adhesive 83, for example, a silicone glue, is applied to the balloon wall at the points where the suture passes through the balloon wall, to preserve the integrity and inflatability of the balloon. As discussed, a tear in the balloon wall can be caused by applying a pulling force on the grasped bead. This same bead formation can also be used to facilitate grasping and removing a device according to the invention, once the anchoring system, if used, has been released from the stomach wall site.

Alternatively, a suture loop extending from the balloon surface can be formed in a like manner, with the exception that a bead is not included. This suture loop can likewise be easily grasped, e.g., by a grasping tool advanced through an endoscope, and used to facilitate manipulation of the device.

FIG. 11 shows a device having tab 91 secured to the balloon surface which likewise serves as a means for grasping and manipulating the balloon. The tab 91 can be secured to the balloon wall by an adhesive, with a portion of the tab extending from the balloon surface for grasping. In a preferred embodiment, the balloon is urethane with a silicone-coating, as further described herein, and the patch is a silicone tab secured to the balloon with an adhesive such as RTV adhesive. By securing the patch to the outer surface of the balloon, the integrity of the balloon wall is preserved.

Modification of the tab and corresponding attachment area of the balloon can also be made to provide relative areas of strength or weakness in the overall balloon surface. In particular, the patch system described can be configured such that it functions as a deflation mechanism. As shown, tab 91 covers weakened portion 93 and strengthened portion 94 of the balloon wall. For example, by heat sealing the patch to the balloon with heat source located on the balloon side, the patch is both secured to the balloon and the weakened portion of the balloon is simultaneously formed. The weakened portion can also be created by, scoring, etching or otherwise thinning the balloon wall. The strengthened portion can be created by reinforcing, thickening, taping, or adhering additional material to the balloon surface. Such strengthening of sections of the balloon can also be accomplished with the combination with a tab, in order to strengthen and/or enhance the structural integrity of the balloon. In the configuration shown in FIG. 12, the application of an upward force to patch 91 at the extended portion 95 will promote a controlled tearing of the balloon wall at the point of least resistance, i.e., weakened portion 93. In this manner, the balloon can be deflated. In addition, the balloon may also be removed by further force on the same grasped tab. In a preferred method where the tab is secured to the balloon by a heat sealing method, by adjusting the heat sealing pattern, the tab can be secured in such a manner that the formed weakened portion of the balloon will be susceptible to tearing, but other portions of the secured tab will be predisposed to remaining attached to the balloon. In such a manner, grasping and pulling on the tab can rupture the balloon to cause deflation yet still allow for removal and manipulation of the balloon by the same grasped tab.

Patch 99 is provided to reinforce the balloon at the suture attachment point, and to also provide for smoother surface at the suture attachment point to lessen irritation to the stomach wall upon attachment. The patch can be secured to the balloon with an adhesive, like tab 91, and can be formed of, e.g., urethane or other similar material, and can further have a silicone coating.

FIG. 12 depicts another embodiment of the invention that provides for a grasping feature. In this embodiment, band 96 extends around the circumference of the balloon, and includes protrusions 97 that extend from the band for grasping and manipulating the balloon. The band can be formed of materials such as those described above for tab 91 and can likewise be adhered to the balloon. The protrusions 97 can be of a variety of shapes. In the depicted embodiment, they are simply folded portions of the band itself.

In an alternative embodiment of the device, device 60 can be of a toroidal configuration, as depicted in FIG. 20. This toroidal configuration can have a variety of annular cross-sectional shapes, including round, elliptical, and the like. The advantage of such configurations is that the beads, guides, suture loops, and tabs described above can be positioned along those areas the surface areas of the device that line the passageway through the center of device formed by the toroidal shape of the device. In this position, these beads, guides, loops, patches, etc. are kept away from the stomach tissue, which lessens the chance of stomach lining irritation and/or erosion such devices could cause when located on the outer diameter of the device. Also, the addition of such a passageway can also aid in the passage of food through the stomach when the device is deployed, lessening the potential of the device to clog the patient's pylorus. In addition, as shown in FIG. 20, suture loops 62 can be secured to the device by passing the suture through the passageway and tying it off around the device. These loops can be easily grabbed by a grasping tool to manipulate the device.

Other portions of a device according to the invention, such as a flange, if provided, or other additional materials, may operate or encompass a strain relief mechanism to accommodate and disperse the forces accompanying any movement of the device attendant due to, e.g., the effects of stomach wall motion of the implanted device.

In particular, a strain relief mechanism functions to reduce strain on the stomach wall at the suture points and to more evenly spread the strain or forces extended on the stomach wall by the device over a broader area. One such strain relief mechanism comprises one or more soft silicone cups, with the rim of the cup being adapted to press against the inside of the stomach wall around the points of suture. In addition, a strain relief mechanism may also be applied against the external stomach wall, such as a strip of polypropylene mesh, or other compliant material to provide a more secure means of attachment against the outer stomach wall. A pledget or tie ff button or similar device may also be used to accomplish the same effect, as is known in the art.

In addition, FIG. 26 illustrates a cross sectional view of a space occupying device that incorporates internal baffle structures 201A and 201B that are formed integrally with the outer member 140, or may be a separate structure. Baffles 120A and 120B operate to distribute any internal inflation media within the space occupying device, thereby decreasing any discomfort to the patient caused by the weight and movement of the device once anchored to the stomach wall. These baffle devices can be in the form of separate compartments, foam materials, gel-type materials or fibers, that can be inserted into the space occupying device either pre- or post-deployment, depending on the insertion profile desired.

Figure 17:
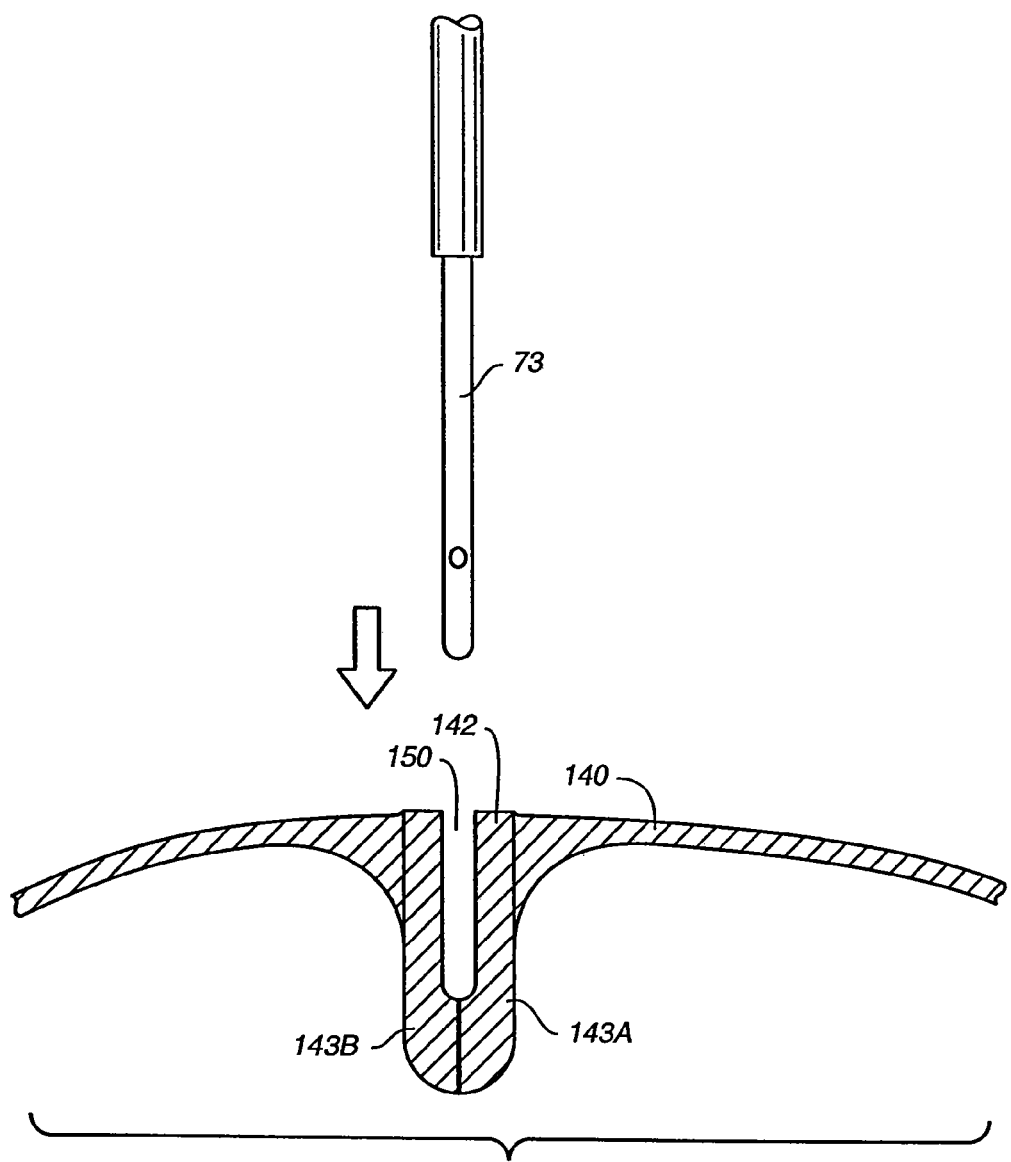
FIG. 17 shows a detailed view of the valve configuration of the device of FIG. 15, with parts broken away, and an inflation needle positioned to engage the valve.

As shown in FIG. 17, valve device 142 facilitates the expansion and contraction of the space occupying device. Valve device 142 includes reception chamber 150 for receipt of an inflation needle 73, and having chamber walls 143A and 143B molded into a single piece and glued or otherwise attached within the layers of outer member 140. The valve device may be affixed within space occupying device 70 in various ways, including gluing, threading, heat sealing or installation of a small hose clamp to secure the valve body.

Valve device 142 can, but need not, have dimensions including an overall width of 0.24", and an overall length of 0.65". The reception chamber has a dimension of preferably 0.070" wide by 0.44" in length, allowing for a portion of the valve to be solid material, subject only to a puncture by a needle or other sharp inflation tool such as inflation needle 73.

As also discussed above, a pre-assembled sharp needle and syringe with check valve combination may be used to inflate the device. In addition, the valve employed in such a case can be a one-way valve known in the art that is self-closing upon removal of the needle. It is also advantageous, in such cases, to include a cylindrically shaped valve guard (not shown) extending inwardly of the balloon at the valve site. This valve guard can be formed of a variety of materials, such as a hard plastic, and serves to avoid inadvertent puncturing of the balloon by the sharp needle upon installation and deployment of the device.

Another method of forming the device with an integral valve is depicted in FIGS. 18A-18C. In this method complimentary sheets of balloon material, such as urethane, are aligned and heat sealed together along their perimeter, as depicted in FIG. 18A. The sheet configuration and heat sealing pattern yields valve portion 42 and anchor suture attachment portion 43. The heat sealed unit is then inverted, as depicted in FIG. 18B-18C, and anchoring suture 71 is then heat sealed to anchoring suture attachment portion 43 of the formed balloon. The formed valve of the balloon is self-closing upon removal of an inflation needle after inflation.

Complications of prior art devices have included erosion or irritation of the stomach wall. These are overcome by the combination of elements present in the described invention, namely that the space occupying device is not free to float about the stomach causing such damage, but is secured in a specific location where design features can minimize such complications. It is further contemplated by the present invention that the expandable member may be lined, or otherwise reinforced with the same or different material to guard against leak or deflation, and also to provide for a conformable outer surface, further decreasing the side effect of erosion. For example, the expandable member may be formed of silicone or another material having conformable, compliant characteristics, and be lined with a second material such as urethane, that has a low porosity to provide for longer inflation, but may be more rigid thereby increasing the risk of erosion.

Similarly, the expandable member may be formed of a lower porosity material, and then "dipped" or coated with a more compliant or pliable material to achieve a similar effect. It is also contemplated that the same configuration can be achieved by placing one structure of one material inside the other structure of another material prior to expansion.

Inflation/Expansion Media

The invention further provides an inflation or expansion media that is of low density and which also poses a low risk or toxicity to the patient should the space occupying device become compromised, either accidentally during deployment or residence within the stomach, or intentionally, due to rupture attendant to removal of the device. A space occupying device according to the invention can be inflated or expanded with various media including, air, water (H2O), carbon dioxide, argon gas, helium or other inert gas, saline, certain slurries or other viscous materials such as mineral oil (and combinations of the foregoing with a mineral oil solution), glass beads, Perlite®, suture material (e.g. prolene, nylon or other space occupying material that can be rendered sterile), and organic material, such as seeds (e.g. poppy, sesame, wheat, bean, pysillium), xanthum gum, and the like. Organic material may pose less of a threat to the patient in a situation where rupture of the space occupying device may occur. The filling material may also include barium sulfate (BaSO4) or a similar agent so it can be seen on x-ray; or blue dye, such as methylene blue, such that the patient would notice a change in urine color that would signify a leak or other break in the device barrier. In addition, if the mechanism for removal requires deflation of the volume, it may be advantageous to intentionally rupture the space occupying device to assist removal.

Inflation/Expansion Elements

In it a further object of the invention to provide for an expansion or inflation media or element, that is independent of leaks or other disruption to the expandable member of the space occupying device. This aspect of the invention provides for an outer member coupled with an inner member, the inner member being adapted to operate independently from the outer member but intended to be enclosed by the outer member at the point of initial deployment of the device. This inner member can include a variety of configurations such as an internal structure that is a predetermined shape, a random shape, a manually actuated element, or a liner.

Predetermined Shape

In the embodiment depicted in FIG. 21 a formation is inserted into the expandable member 140 through valve structure 142. Expandable member 140 can be an expandable membrane, such as a balloon, or other expandable material such as graft material or other like covering. Inner member 170 is preferably a resilient structure, such as a wire form made from stainless steel, NiTi, Elgiloy, semi-rigid polymer, or other such material, that can be inserted into the expandable member yet maintain its shape independent of the integrity of the expandable member. During removal, it is contemplated by the present invention that inner member 170 can be removed by extraction through valve member 142, as in the case of the more rigid members such as those made of metal or metal composites (e.g. NiTi, Elgiloy™ or stainless steel), or released into the stomach cavity through disruption of the expandable member as in the less rigid, but filling inner members (e.g. suture, polymers).

Expandable Shell with Random Internal Structure

In another embodiment of the present invention, as shown in FIG. 22, inner member 171 comprises a random matrix of material, such as a linear structure that has no predetermined shape but rather forms a randomly arranged matrix upon introduction into the expandable member. This material can include wire made of a low profile NiTi wire, for example 0.020" diameter, braided suture material, or other material, such as stainless steel, Elgiloy™ alloy, or a pliable polymer matrix such as polypropylene, polyethylene or polycarbonate. This inner member may be placed in various ways, such as through a catheter device 172 by using a pusher assembly 173, to deploy the inner member through valve 142, such that it reforms a random, space filling shape, within expandable member 140. The present invention also contemplates that the random inner member may comprise a single strand of material to facilitate removal, or multiple strands or composites of a material to optimize the filling of the space occupying device.

FIG. 22 depicts the deployment of inner member 171 via a transabdominal approach once the space occupying device of the present invention is secured at the anchoring point (AP), but it is also within the scope of the present invention to deploy the inner member 171 via the transesophageal approach. It is likewise within the scope of the invention to deploy inner member 170 of FIG. 21 via the transabdominal approach.

Expandable Shell with Manually Deployed Inner Structure

FIG. 24 illustrates a device having an inner member 180 that is inserted through valve opening 142 in a contracted configuration, and then expanded into an expanded configuration by manual manipulation by the placing physician. The inner member includes a central shaft 181 to which the distal ends of a manual expansion element 182 and cap DE by means of welding, gluing or other such attachment means. Movable shaft 183, which has the ability to movably translate with regard to central shaft 181 is placed coaxial around said central shaft 181. The proximal ends of the manual expansion element are affixed to the movable shaft 183, such that when said movable shaft 183 is advanced toward the point DE, manual expansion elements 182 bow outwardly toward to effect an expanded configuration coterminous with expandable member 140. The proximal ends of said expansion elements 182, are similarly affixed in a coaxial configuration to movable shaft 183, such that the entire expandable element 180 fits within expandable member 140.

Monitoring Placement

Once the space occupying device of the present invention has been placed, it is advantageous for the physician to be able to monitor the placement and integrity of the device in a minimally invasive way. To enable non-invasive monitoring, a feature of the present invention includes providing a radiopaque grid or pattern 190 permanently affixed to the space occupying device, as depicted in FIG. 25. The grid 190 may be printed on or embedded within the layers of the outer member. In this embodiment, a pattern is printed with an ink made of tungsten powder and glue, or thin strips of Copper, lead or stainless steel, and may measure 0.10"×0.001". These markings can then be affixed to the space occupying device either internally, externally or laminated between the layers of the space occupying device during construction. In addition, the space occupying device may be filled with inflation media that includes BaSO4. Alternatively, a small pressure transducer (not shown) with a radio transmitter may be placed in the space occupying device to continuously send data to an external monitor (not shown). Under x-ray vision, the physician can monitor both the placement (e.g. is the device still properly anchored against the stomach wall or other structure) and the integrity (e.g. is the device still expanded) of the space occupying device. This monitoring procedure may be done proactively, or as a diagnostic measure in the event a patient presents with symptoms relating to loss of efficacy or physical complications.

In Situ Modification

An important feature of the present invention is the ability to modify the volume of the space occupying device once it is implanted in the patient's stomach. This is advantageous for a variety of reasons to maximize the efficacy of the device for a particular patient. During implantation, a patient may find that their hunger returns, or is more than they would like. With a device of the present invention this can be accomplished either through a transesophageal approach, or through the installation of a PEG tube at the site of anchor. FIGS. 27A and 27B illustrate one such embodiment, depicting a docking port 210 for a space occupying device having a flange 141 and a valve with filling lumen 212. FIGS. 27C-27F illustrates a docking module 214 configured to fit coaxially over the end of a conventional endoscope (ES). Docking module 214 incorporates a snare housing 216 with a lumen to house a snare device (SD). In operation, for transesophageal access, the endoscope and docking module are inserted down the patient's throat to the vicinity of the docking port 210. Snare device (SD) is used, under direct vision of the endoscope, to grasp gripping flange 141 and guide the docking module 214 to mating engagement with docking port 210. Stops 217 can be included on the inner channel of the docking module to restrain the endoscope. An inflation device (not shown) can then be introduced through the endoscope and inserted into filling lumen 212 to further inflate, or deflate the space occupying device as desired. An optional feature of the docking module is an alignment target (not shown) that cooperates with a point on the space occupying device, either electronically, visually (i.e., a marker), or physically (i.e., a detent or other configuration), to assist in alignment of the docking module with the docking port.

In another inventive method, in situ modification of the device volume can be adjusted through the use of an implanted subcutaneous port 175, placed in the arm, stomach or pectoral area of the patient, as depicted in FIG. 23. Typical ports used for drug delivery are the BARDPORT® implanted ports (Bard Access Systems, Salt Lake City, Utah) and the VORTEX™, TRIUMPH-1®, LIFEPORT® and INFUSE-A-PORT® implanted ports (Horizon Medical Products, Manchester, Ga.). For use in the present invention, such ports may be modified, according to ways known in the art, to provide a more durable septum to accommodate a lower gauge needle and a larger lumen catheter that are desirable for the more efficient ingress or egress of air, gas or other inflation media into or from the device.

While certain embodiments have been illustrated and described, those having ordinary skill in the art will appreciate that various alternatives, modifications, and equivalents may be used and that the invention is not intended to be limited to the specifics of these embodiments, but rather is defined by the accompanying claims.

We claim:

1. A method of deploying a space occupying device into the stomach of a patient comprising the steps of:
    creating an opening into the stomach of the patient;
    inserting a guidewire through said opening, such that a first end of said guidewire is located within the patient's stomach and a second end of said guidewire remains external to the patient;
    introducing a grasping tool into the patient's mouth, through the patient's throat, and esophagus and into the patient's stomach;
    grasping said first end of said guidewire with said grasping tool;
    removing the grasping tool from the patient's stomach, through the patient's esophagus and throat and out the patient's mouth, thereby locating said first end of said guidewire outside the patient's mouth;
    providing a space occupying device and securing said one first end of said guidewire to said space occupying device;
    applying a force to said second end of said guidewire thereby pulling said device into the patient's mouth, through the patient's throat and esophagus, and into the patient's stomach;
    inflating the space occupying device through an inflation tube passed through the patient's throat and esophagus, the inflation tube comprising a needle sized to cooperate with a reception chamber of a valve on the space occupying device; and
    withdrawing the inflation tube through the patient's throat and esophagus once the space occupying device is inflated.

2. The method of claim 1 wherein said step of creating a surgical opening further comprises creating a gastric fistula.

3. The method of claim 1 further comprising the step of using an endoscope to visualize or indicate a site for creating said surgical opening.

4. The method of claim 1 wherein said step of introducing said grasping tool further comprises the step of inserting an endoscope into the patient's mouth, through the patient's throat and esophagus, and into the patient's stomach and then advancing the grasping tool through the endoscope.

5. The method of claim 1 wherein said grasping tool is a snare.

6. The method of claim 1 wherein said space occupying device further comprises one or more sutures secured to said device, and wherein said securing step further comprises securing said one or more sutures to said guidewire.

7. The method of claim 6 further comprising the step of suturing said one or more sutures to the patient's stomach wall.

8. The method of claim 1 wherein said space occupying device is inflatable and further comprising the step of inflating said device after insertion into the patient's stomach.

* * * * *